United States Patent
Ookubo et al.

(10) Patent No.: US 9,540,338 B2
(45) Date of Patent: Jan. 10, 2017

(54) SUBSTITUTED CINNAMIC ACID AMIDES FOR TREATING PAIN

(71) Applicant: NIPPON ZOKI PHARMACEUTICAL CO., LTD., Osaka-shi, Osaka (JP)

(72) Inventors: Tomohiro Ookubo, Kato (JP); Ko Nakamura, Kato (JP); Yoshitaka Nakazawa, Kato (JP); Hiroyoshi Nanba, Kato (JP); Hiroyuki Yoshida, Kato (JP)

(73) Assignee: NIPPON ZOKI PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 14/652,978

(22) PCT Filed: Dec. 27, 2013

(86) PCT No.: PCT/JP2013/085041
§ 371 (c)(1),
(2) Date: Jun. 17, 2015

(87) PCT Pub. No.: WO2014/104272
PCT Pub. Date: Jul. 3, 2014

(65) Prior Publication Data
US 2015/0322024 A1  Nov. 12, 2015

(30) Foreign Application Priority Data
Dec. 28, 2012 (JP) .................. 2012-286935

(51) Int. Cl.
| | |
|---|---|
| *A61K 31/16* | (2006.01) |
| *C07C 233/01* | (2006.01) |
| *C07D 295/13* | (2006.01) |
| *C07D 209/16* | (2006.01) |
| *C07D 249/08* | (2006.01) |
| *C07D 231/12* | (2006.01) |
| *C07D 231/56* | (2006.01) |
| *C07D 233/64* | (2006.01) |
| *C07D 235/06* | (2006.01) |
| *C07D 249/04* | (2006.01) |
| *C07D 261/08* | (2006.01) |
| *C07D 207/335* | (2006.01) |
| *C07D 209/14* | (2006.01) |
| *C07D 295/12* | (2006.01) |
| *C07D 213/40* | (2006.01) |
| *C07C 279/12* | (2006.01) |
| *C07C 233/51* | (2006.01) |
| *C07C 233/40* | (2006.01) |

(52) U.S. Cl.
CPC ......... *C07D 295/13* (2013.01); *C07C 233/40* (2013.01); *C07C 233/51* (2013.01); *C07C 279/12* (2013.01); *C07D 207/335* (2013.01); *C07D 209/14* (2013.01); *C07D 209/16* (2013.01); *C07D 213/40* (2013.01); *C07D 231/12* (2013.01); *C07D 231/56* (2013.01); *C07D 233/64* (2013.01); *C07D 235/06* (2013.01); *C07D 249/04* (2013.01); *C07D 249/08* (2013.01); *C07D 261/08* (2013.01); *C07D 295/12* (2013.01); *C07C 2101/14* (2013.01)

(58) Field of Classification Search
CPC .............................. A61K 31/16; C07C 233/01
USPC .......................................... 514/617; 564/204
See application file for complete search history.

(56) References Cited

U.S. PATENT DOCUMENTS

| | | | |
|---|---|---|---|
| 4,568,687 A | 2/1986 | Wright, Jr. et al. | |
| 7,582,657 B2 | 9/2009 | Chen et al. | |
| 2004/0087798 A1* | 5/2004 | Yamada | ............... C07C 205/12 546/336 |
| 2004/0106621 A1 | 6/2004 | Wu et al. | |
| 2004/0122007 A1 | 6/2004 | Wu et al. | |
| 2009/0149658 A1 | 6/2009 | Nakamura et al. | |
| 2010/0292229 A1 | 11/2010 | Donato et al. | |

FOREIGN PATENT DOCUMENTS

| | | |
|---|---|---|
| JP | S50-30842 A | 3/1975 |
| JP | S59-164779 A | 9/1984 |
| JP | 2007-210974 A | 8/2007 |
| JP | 2012-510512 A | 5/2012 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Oliff PLC

(57) ABSTRACT

A cinnamic acid amide derivative having an excellent analgesic action is disclosed herein. The cinnamic acid amide derivative shows excellent analgesic actions to not only a nociceptive pain model animal, but also a neuropathic pain model animal, which is very useful as an agent for treating various pain diseases showing acute or chronic pains or neuropathic pains. The cinnamic acid amide derivative may be a compound represented by formula (I).

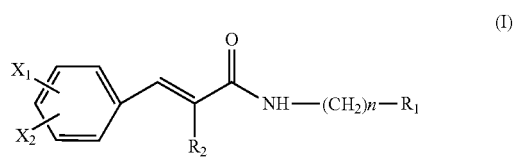

19 Claims, No Drawings

(56) References Cited

FOREIGN PATENT DOCUMENTS

| WO | 2008/005954 A2 | 1/2008 |
|---|---|---|
| WO | 2008/152097 A1 | 12/2008 |
| WO | 2009/008997 A2 | 1/2009 |
| WO | 2012/177618 A1 | 12/2012 |

OTHER PUBLICATIONS

Vippagunta, et al. Advanced Drug Delivery Reviews, 48, 2001, 18.*
Berg, et al. Bioorganic & Medicinal Chemistry, 15(11), 2007, 3692-3702.*
McCluskey et al., "Green Chemistry Approaches to the Knoevenagel Condensation: Comparison of Ethanol, Water and Solvent Free (Dry Grind) Approaches," Tetrahedron Letters, 2002, vol. 43, pp. 3117-3120.
Wu et al., "Synthesis and Structure Activity Relationship of Acrylamides as KCNQ2 Potassium Channel Openers" J Med. Chem., 2004, vol. 47, No. 11, pp. 2887-2896.
[Online]STN on the web Registry, Registry Nos. (RN)1355939-10-4, RN:1049986-43-7.
[Online]STN on the web Registry, Registry Nos. (RN)1390880-10-0, RN:1331431-99-2, RN:1182471-93-7, RN:1051342-50-7. RN:928970-60-9, RN:853347-68-9, RN:329042-56-0.
[Online]STN on the web Registry, Registry Nos. RN:1173545-05-5, 1173523-24-4.
[Online]STN on the web Registry, Registry Nos. RN:1268315-16-7, RN:1158136-28-7, 1158117-61-3.
[Online]STN on the web Registry, Registry Nos. RN:1369422-91-2, RN:1286387-31-2, RN:1276099-01-4, RN:1251433-64-3, RN:1251408-58-8, RN:1158140-73-8, RN:1097788-50-5.
[Online]STN on the web Registry, Registry Nos. RN:464909-19-1, RN:1308784-76-0, RN:1216364-19-0, RN:1198071-08-7, RN:1379398-19-2, RN:1216355-19-9 RN:1390912-62-5 RN:1331540-63-6' RN:528532-89-0, RN:1276072-30-0, RN:932251-41-7 RN:1308867-77-7, RN:1259228-62-0, RN:928947-11-9, RN:1372390-79-8, RN:1331430-20-6, RN:550351-46-7.
Feb. 25, 2014 International Search Report issued in International Patent Application No. PCT/JP2013/085041.
Kim et al., "An Experimental Model for Peripheral Neuropathy Produced by Segmental Spinal Nerve Ligation in the Rat," Pain, 1992, vol. 50, pp. 355-363.
Chaplan et al., "Quantitative Assessment of Tactile Allodynia in the Rat Paw," Journal of Neuroscience Methods, 1994, vol. 53, pp. 55-63.
Pau, A. et al., "Synthesis of 1-methyl-4-(n-aroyl)-piperidinamides with Anti-inflammatory and Analgesic Activities," IL Farmaco, 1998, vol. 53, pp. 233-240.
Jul. 13, 2016 Office Action issued in Singapore Application No. 11201505120U.
Chemical Abstract Service (CAS) Registry No. 1281683-83-7.

* cited by examiner

SUBSTITUTED CINNAMIC ACID AMIDES FOR TREATING PAIN

TECHNICAL FIELD

The present invention relates to a cinnamic acid amide derivative or a pharmaceutically acceptable salt thereof. Also, the present invention relates to a pharmaceutical agent such as an analgesic, containing, as an active ingredient, at least one member of the compound and a pharmaceutically acceptable salt thereof.

BACKGROUND

"Pains" are roughly classified by causes of diseases into nociceptive pain (so-called general "pain") caused by a strong stimulus (nociceptive stimulus) that would result in damages to body tissues, and neuropathic pain, which is a disease pain resulting from an injury or malfunction of the central or peripheral nerve. This neuropathic pain causes, in addition to a spontaneous pain, a symptom such as a hyperalgesia that lowers the pain thresholds against the nociceptive stimulus and a severe pain (allodynia) caused by tactile stimulation that usually does not induce the pain. Once the morbid state is completed, it turns chronically whereby the outcome is very intractable.

At present, non-steroidal anti-inflammatory drugs (NSAIDs), non-narcotic analgesics, narcotic analgesics, and the like are used against general "pains," so that therapeutic methods therefor have begun to be established. However, there are hardly any analgesics that can satisfy the neuropathic pains under the current situation.

As a result of intensive studies on the compounds that show effects on various pains, the present inventors have found that the cinnamic acid amide derivative of the present invention has excellent analgesic actions to not only a nociceptive pain model animal but also a neuropathic pain model animal. As cinnamic acid amide derivatives, Patent Publication 1 discloses a compound having antidepressant action and analgesic action. However, only the effects on nociceptive pains are evaluated, and actions on chronic pains such as neuropathic pains are not described at all.

PRIOR ART REFERENCES

Patent Publications

Patent Publication 1: Japanese Patent Laid-Open No. Sho-50-30842

SUMMARY OF THE INVENTION

Problems to be Solved by the Invention

An object of the present invention is to provide a cinnamic acid amide derivative which is useful as a pharmaceutical agent such as an analgesic.

Means to Solve the Problems

As a result of intensive studies on compounds showing effects against various pains, the present inventors have found that a cinnamic acid amide derivative represented by the following general formula (I) has an excellent analgesic action in a model animal for nociceptive pains and a pathological model animal for neuropathic pains, so that the cinnamic acid amide derivative is useful as a pharmaceutical agent such as an analgesic. The present invention has been perfected thereby.

Effects of the Invention

The cinnamic acid amide derivative of the present invention is a compound that shows excellent analgesic actions at low doses to not only a model animal for nociceptive pains but also a model animal for neuropathic pains, so that the cinnamic acid amide derivative is very useful as a drug for treating various pain diseases and the like.

DETAILED DESCRIPTION

The present invention relates to a novel cinnamic acid amide derivative or a pharmaceutically acceptable salt thereof, wherein the cinnamic acid amide derivative is represented by the following general formula (I):

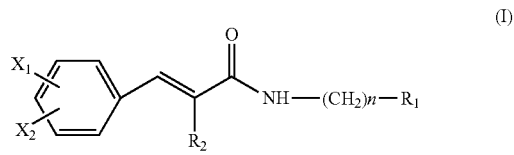

(I)

wherein n stands for an integer of from 0 to 4;

$X_1$ and $X_2$, which are identical or different, stand for a hydrogen, a fluorine, a trifluoromethyl, or a carboxy, and either one of $X_1$ and $X_2$ stands for a substituent other than a hydrogen;

$R_1$ stands for:

an imidazolyl which may be substituted with alkyl having 1 to 6 carbon atoms or phenyl;

a pyrrolyl which may be substituted with alkyl having 1 to 4 carbon atoms;

a phenyl substituted with amino, alkoxy having 1 to 4 carbon atoms, pyrazolyl, isoxazolyl or morpholino;

a phenyl substituted with thiomorpholino which may be substituted with oxo;

a piperazino which may be substituted with alkyl having 1 to 4 carbon atoms or cyclohexyl;

a thiomorpholino which may be substituted with one or two oxos;

an amino which may be substituted with one or two alkyls having 1 to 4 carbon atoms; or any one of substituents selected from guanidino, benzoimidazolyl, indazolyl, pyrazolyl, triazolyl, pyridyl, pyrrolidinyl, piperidino, hexamethyleneimino, morpholino, and cyclohexylamino; and $R_2$ stands for a hydrogen, a cyano or an alkyl having 1 to 4 carbon atoms, with proviso that in a case of n=0, $R_1$ stands for a substituent other than a phenyl substituted with morpholino; in a case of n=1, $R_1$ stands for a substituent other than a pyridyl; in a case where $R_1$ is a morpholino and $R_2$ is a hydrogen, when either one of $X_1$ and $X_2$ is a hydrogen, the other stands for a substituent other than a fluorine.

In addition, the present invention relates to a pharmaceutical agent such as an analgesic, containing, as an active ingredient, at least one member of a cinnamic acid amide derivative and a pharmaceutically acceptable salt thereof, wherein the cinnamic acid amide derivative is represented by the following general formula (I):

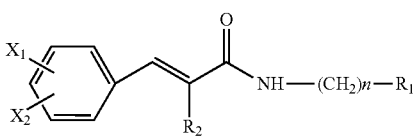

(I)

wherein n stands for an integer of from 0 to 4;

$X_1$ and $X_2$, which are identical or different, stand for a hydrogen, a fluorine, a trifluoromethyl, or a carboxy, and either one of $X_1$ and $X_2$ stands for a substituent other than a hydrogen;

$R_1$ stands for:

an imidazolyl which may be substituted with alkyl having 1 to 6 carbon atoms or phenyl;

a pyrrolyl which may be substituted with alkyl having 1 to 4 carbon atoms;

a phenyl substituted with amino, alkoxy having 1 to 4 carbon atoms, pyrazolyl, isoxazolyl or morpholino;

a phenyl substituted with thiomorpholino which may be substituted with oxo;

a piperazino which may be substituted with alkyl having 1 to 4 carbon atoms or cyclohexyl;

a thiomorpholino which may be substituted with one or two oxos;

an amino which may be substituted with one or two alkyls having 1 to 4 carbon atoms; or any one of substituents selected from carboxy, guanidino, indolyl, benzoimidazolyl, indazolyl, pyrazolyl, triazolyl, pyridyl, pyrrolidinyl, piperidino, hexamethyleneimino, morpholino, and cyclohexylamino; and $R_2$ stands for a hydrogen, a cyano or an alkyl having 1 to 4 carbon atoms.

In the substituents of the general formula (I) mentioned above, the alkyl having 1 to 4 carbon atoms stands for a linear or branched alkyl group, and the alkyl group is preferably a methyl, an ethyl, a propyl, an isopropyl, a butyl, an isobutyl, a sec-butyl, a t-butyl, or the like. The alkyl having 1 to 6 carbon atoms stands for a linear or branched alkyl group, and the alkyl group is preferably, a methyl, an ethyl, a propyl, an isopropyl, a butyl, an isobutyl, a sec-butyl, a t-butyl, a pentyl, an isopentyl, a neopentyl, a t-pentyl, a hexyl, an isohexyl or the like. The alkoxy having 1 to 4 carbon atoms stands for a linear or branched alkoxy group, and the alkoxy group is preferably a methoxy, an ethoxy, an n-propoxy, an isopropoxy, an n-butoxy, an isobutoxy, a sec-butoxy, a t-butoxy, or the like.

The above-mentioned compound of the present invention represented by the general formula (I) can be produced in accordance with a method of (1) or (2) mentioned hereinbelow. However, during the production of a specified compound, one of ordinary skill in the art can as a matter of course modify properly in accordance with the chemical structures thereof.

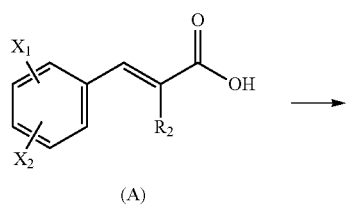

(A)

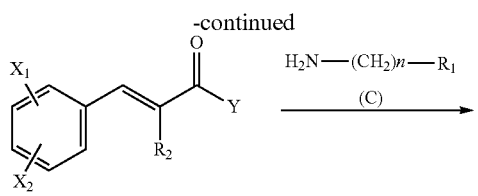

(B)

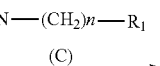

(C)

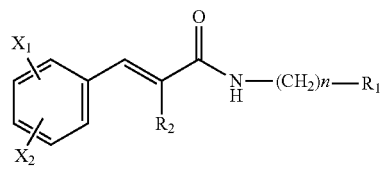

(D)

(1) Active Ester Method

A compound of the general formula (B) [where Y is a cyanomethylhydroxy, a p-nitrophenoxy, a halogen-substituted phenoxy (a 1,3,5-trichlorophenoxy, a pentafluorophenoxy, etc.), a 2,5-dioxopyrrolidin-1-yloxy (HOSu), a 1,3-dioxo-1,3-dihydroisoindol-2-yloxy, a 3,5-dioxo-4-azatricyclo[5.2.1.0$^{2,6}$]-8-decen-4-yloxy (HONB), a quinolin-8-yloxy, or a pyridin-2-yloxy], which is an active ester form, can be obtained by reacting a compound of the general formula (A) with a suitable activating reagent in the presence of a suitable condensing agent in a solvent which is inert to the reaction, at room temperature for usually 1 to 24 hours. A compound of the general formula (D) can be obtained by reacting the compound of the general formula (B) and a compound of the general formula (C) in a solvent which is inert to the reaction, in the presence of an inorganic base such as sodium hydrogencarbonate, potassium hydrogencarbonate, sodium carbonate, or potassium carbonate, at room temperature for usually 1 to 30 hours. Here, the inert solvent includes, for example, halogenated hydrocarbon-based solvents such as dichloromethane, 1,2-dichloroethane, and chloroform; ether-based solvents such as tetrahydrofuran (THF), 1,4-dioxane, 1,2-dimethoxyethane, and diethyl ether, and the like, or a mixed solvent such as acetonitrile-water, 1,4-dioxane-water, or tetrahydrofuran (THF)-dimethyl formamide (THF-DMF) may be used. The condensing agent includes water-soluble carbodiimide (WSC.HCl), dicyclohexylcarbodiimide (DCC), DCC-1-hydroxybenzotriazole (DCC-HOBt), carbonyldiimidazole (CDI), and the like, and the activating reagent includes N-hydroxysuccinic acid imide, phenol, p-nitrophenol, and the like. The compound of the general formula (B), which is an active ester form, can also be obtained by reacting an acid chloride mentioned later with HOSu or the like in a solvent which is inert to the reaction, in the presence of an organic base such as triethylamine or N-methylmorpholine, at room temperature for usually from 1 to 30 hours.

(2) Acid Chloride Method

A compound of the general formula (B) [where Y is a halogen such as fluorine, chlorine, bromine, or iodine] is formed by reacting a compound of the general formula (A) with a suitable halogenating reagent at a temperature equal to or lower than room temperature in an anhydrous solvent inert to the reaction. A compound of the general formula (D) can be obtained by adding a compound of the general formula (C) to the compound of the general formula (B) isolated or without being isolated at a temperature of 0° C. or lower or a temperature equal to or lower than room temperature, and reacting the compounds for usually 1 to 30 hours. Here, the inert anhydrous solvent includes, for example, halogenated hydrocarbon-based solvents such as dichloromethane, 1,2-dichloroethane, and chloroform; ether-based solvents such as tetrahydrofuran (THF), 1,4-dioxane, 1,2-dimethoxyethane, and diethyl ether; aromatic hydrocarbon-based solvents such as benzene, toluene, and xylene; and the like. In addition, the suitable halogenating reagent includes cyanuric fluoride, phosphorus trichloride, phosphorus pentachloride, thionyl chloride, oxalyl chloride, cyanuric chloride, cyanuric bromide, dibromotriphenyl-phosphorane, 1-dimethylamino-1-iodo-2-methylpropene, and the like.

The compound represented by the general formula (I) mentioned above includes, in a case where a pharmaceutically acceptable salt thereof is present, various kinds of salts thereof. The salts include, for example, addition salts with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, or sulfanilic acid; salts with metals, such as alkali metals such as sodium and potassium, alkaline earth metals such as calcium and magnesium, or aluminum; or salts with bases such as ammonia and organic amines. These salts can be produced from each compound in a free form, or converted reversibly, in accordance with a known method. In addition, in a case where the compounds are present in the state of a stereoisomer such as a cis-trans isomer, an optical isomer or a coordination isomer, or a solvate including a hydrate or a metal complex compound, the present invention embraces any of stereoisomers, solvates, and complex compounds.

Among the compounds of the present invention, preferred compounds are as follows.

(E)-3-(2-Fluorophenyl)-N-[2-(1H-indol-3-yl)ethyl]-2-propenamide [Compound 1];
(E)-3-(2-Fluorophenyl)-N-(3-pyridylmethyl)-2-propenamide [Compound 2];
(E)-3-(2-Fluorophenyl)-N-[2-(4-pyridyl)ethyl]-2-propenamide [Compound 3];
(E)-3-(2-Fluorophenyl)-N-[2-(1-piperidyl)ethyl]-2-propenamide [Compound 4];
(E)-3-(2-Fluorophenyl)-N-(2-morpholinoethyl)-2-propenamide [Compound 5];
(E)-N-[2-(4-Cyclohexylpiperazin-1-yl)ethyl]-3-(2-fluorophenyl)-2-propenamide [Compound 6];
(E)-N-[3-(4-Cyclohexylpiperazin-1-yl)propyl]-3-(2-fluorophenyl)-2-propenamide [Compound 7];
(E)-3-(2-Fluorophenyl)-N-[2-(1-methyl-1H-pyrrol-2-yl)ethyl]-2-propenamide [Compound 8];
(E)-3-(2-Fluorophenyl)-N-[2-(2-pyridyl)ethyl]-2-propenamide hydrochloride [Compound 9];
(E)-3-(2-Fluorophenyl)-N-[2-(3-pyridyl)ethyl]-2-propenamide hydrochloride [Compound 10];
(E)-3-(2-Fluorophenyl)-N-(3-morpholinopropyl)-2-propenamide hydrochloride [Compound 11];
(E)-N-(3-Dimethylaminopropyl)-3-(2-fluorophenyl)-2-propenamide hydrochloride [Compound 12];
(E)-N-(4-Dimethylaminobutyl)-3-(2-fluorophenyl)-2-propenamide hydrochloride [Compound 13];
(E)-N-(4-Aminobutyl)-3-(2-fluorophenyl)-2-propenamide hydrochloride [Compound 14];
(E)-3-(2-Fluorophenyl)-N-[3-(4-methylpiperazin-1-yl)propyl]-2-propenamide dihydrochloride [Compound 15];
(E)-3-(2-Fluorophenyl)-N-[2-(piperazin-1-yl)ethyl]-2-propenamide dihydrochloride [Compound 16];
(E)-3-(2-Fluorophenyl)-N-[3-(piperazin-1-yl)propyl]-2-propenamide dihydrochloride [Compound 17];
(E)-3-(2-Fluorophenyl)-N-[2-(1H-imidazol-4-yl)ethyl]-2-propenamide [Compound 18];
(E)-N-[2-(2-Aminophenyl)ethyl]-3-(2-fluorophenyl)-2-propenamide [Compound 19];
(E)-3-(2-Fluorophenyl)-N-[2-(4-methylpiperazin-1-yl)ethyl]-2-propenamide [Compound 20];
(E)-3-(2-Fluorophenyl)-N-[2-(imidazol-1-yl)ethyl]-2-propenamide hydrochloride [Compound 21];
(E)-N-[2-(Benzoimidazol-1-yl)ethyl]-3-(2-fluorophenyl)-2-propenamide [Compound 22];
(E)-3-(2,4-Difluorophenyl)-N-[2-(imidazol-1-yl)ethyl]-2-propenamide [Compound 23];
(E)-3-(2,5-Difluorophenyl)-N-[2-(imidazol-1-yl)ethyl]-2-propenamide [Compound 24];
(E)-3-(3-Fluorophenyl)-N-(3-morpholinopropyl)-2-propenamide [Compound 25];
(E)-3-(4-Fluorophenyl)-N-(3-morpholinopropyl)-2-propenamide [Compound 26];
(E)-3-(2,3-Difluorophenyl)-N-(3-morpholinopropyl)-2-propenamide [Compound 27];
(E)-3-(2,4-Difluorophenyl)-N-(3-morpholinopropyl)-2-propenamide [Compound 28];
(E)-3-(2,5-Difluorophenyl)-N-(3-morpholinopropyl)-2-propenamide [Compound 29];
(E)-3-(2,6-Difluorophenyl)-N-(3-morpholinopropyl)-2-propenamide [Compound 30];
(E)-3-(3,4-Difluorophenyl)-N-(3-morpholinopropyl)-2-propenamide [Compound 31];
(E)-3-(2-Fluoro-4-trifluoromethylphenyl)-N-(3-morpholinopropyl)-2-propenamide [Compound 32];
(E)-3-(4-Fluorophenyl)-N-[4-morpholinophenyl]-2-propenamide [Compound 33];
(E)-N-(2-Aminoethyl)-3-(2-fluorophenyl)-2-propenamide hydrochloride [Compound 34];
(E)-3-(2-Fluorophenyl)-N-[2-(pyrrolidin-1-yl)ethyl]-2-propenamide [Compound 35];
(E)-N-[(2-Azepan-1-yl)ethyl]-3-(2-fluorophenyl)-2-propenamide [Compound 36];
(E)-3-(2-Fluorophenyl)-N-[2-(4-methoxyphenyl)ethyl]-2-propenamide [Compound 37];
(E)-3-(2-Fluorophenyl)-N-[2-(pyrazol-1-yl)ethyl]-2-propenamide [Compound 38];
(E)-3-(2-Fluorophenyl)-N-[2-([1,2,4]triazol-1-yl)ethyl]-2-propenamide dihydrochloride [Compound 39];
(E)-3-(2-Fluorophenyl)-N-[2-([1,2,3]triazol-1-yl)ethyl]-2-propenamide [Compound 40];
(E)-3-(2-Fluorophenyl)-N-[2-(indol-1-yl)ethyl]-2-propenamide [Compound 41];
(E)-3-(2-Fluorophenyl)-N-[2-(2-methylimidazol-1-yl)ethyl]-2-propenamide [Compound 42];
(E)-3-(2-Fluorophenyl)-N-[2-(2-isopropylimidazol-1-yl)ethyl]-2-propenamide hydrochloride [Compound 43];
(E)-3-(2-Fluorophenyl)-N-[2-(2-phenylimidazol-1-yl)ethyl]-2-propenamide [Compound 44];
(E)-3-(2-Fluorophenyl)-N-[3-(imidazol-1-yl)propyl]-2-propenamide hydrochloride [Compound 45];
(E)-3-(4-Fluorophenyl)-2-methyl-N-(3-morpholinopropyl)-2-propenamide [Compound 46];
(E)-3-(2-Carboxyphenyl)-N-[(2-imidazol-1-yl)ethyl]-2-propenamide [Compound 47];
(E)-3-(2-Fluorophenyl)-N-[2-(2-butylimidazol-1-yl)ethyl]-2-propenamide hydrochloride [Compound 48];

(E)-3-(3-Carboxyphenyl)-N-[(2-imidazol-1-yl)ethyl]-2-propenamide hydrochloride [Compound 49];
(E)-3-(4-Carboxyphenyl)-N-[(2-imidazol-1-yl)ethyl]-2-propenamide hydrochloride [Compound 50];
(E)-3-(2-Fluorophenyl)-N-[4-(2H-pyrazol-3-yl)phenyl]-2-propenamide [Compound 51];
(E)-3-(2-Fluorophenyl)-N-[3-(2H-pyrazol-3-yl)phenyl]-2-propenamide [Compound 52];
(E)-3-(2-Fluorophenyl)-N-[4-(isoxazol-5-yl)phenyl]-2-propenamide [Compound 53];
(E)-3-(2-Fluorophenyl)-N-[3-(isoxazol-5-yl)phenyl]-2-propenamide [Compound 54];
(E)-3-(2-Fluorophenyl)-N-(1H-indazol-6-yl)-2-propenamide [Compound 55];
(E)-3-(2-Fluorophenyl)-N-(1H-indazol-5-yl)-2-propenamide [Compound 56];
(E)-N-(3-Morpholinopropyl)-3-(2-trifluoromethylphenyl)-2-propenamide hydrochloride [Compound 57];
(E)-2-Cyano-3-(4-fluorophenyl)-N-(3-morpholinopropyl)-2-propenamide [Compound 58];
(E) 3-(2-Fluorophenyl)-N-[3-(1-piperidyl)propyl]-2-propenamide hydrochloride [Compound 59];
(E)-3-(4-Fluorophenyl)-N-(3-thiomorpholinopropyl)-2-propenamide [Compound 60];
(E)-3-(2-Fluorophenyl)-N-(3-thiomorpholinopropyl)-2-propenamide hydrochloride [Compound 61];
(E)-N-[3-(1,1-Dioxo-1,4-thiazinan-4-yl)propyl]-3-(2-fluorophenyl)-2-propenamide hydrochloride [Compound 62];
(E)-N-[3-(1,1-Dioxo-1,4-thiazinan-4-yl)propyl]-3-(4-fluorophenyl)-2-propenamide hydrochloride [Compound 63];
(E)-N-[(3-Cyclohexylamino)propyl]-3-(2-fluorophenyl)-2-propenamide hydrochloride [Compound 64];
(E)-3-(2-Fluorophenyl)-N-(4-guanidinobutyl)-2-propenamide hydrochloride [Compound 65];
3-{[(E)-3-(2-Fluorophenyl)-2-propenoyl]amino}propanoic acid [Compound 66];
(E)-3-(4-Fluorophenyl)-N-[3-(1-oxo-1,4-thiazinan-4-yl)propyl]-2-propenamide [Compound 67];
(E)-3-(2-Fluorophenyl)-N-[3-(1-oxo-1,4-thiazinan-4-yl)propyl]-2-propenamide [Compound 68];
(E)-3-(2-Fluorophenyl)-N-[(3-thiomorpholinophenyl)methyl]-2-propenamide [Compound 69];
(E)-3-(2-Fluorophenyl)-N-{[3-(oxo-1,4-thiazinan-4-yl)phenyl]methyl}-2-propenamide [Compound 70]; and
(E)-3-(2-Fluorophenyl)-2-methyl-N-[3-(1-oxo-1,4-thiazinan-4-yl)propyl]-2-propenamide hydrochloride [Compound 71].

Preferred embodiments of the present inventions are given hereinbelow:
(1) A compound or a pharmaceutically acceptable salt thereof, wherein the compound is represented by the following general formula (I):

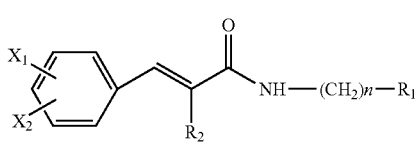

wherein n stands for an integer of from 0 to 4;
$X_1$ and $X_2$, which are identical or different, stand for a hydrogen, a fluorine, a trifluoromethyl, or a carboxy, and either one of $X_1$ and $X_2$ stands for a substituent other than a hydrogen;

$R_1$ stands for:
an imidazolyl which may be substituted with alkyl having 1 to 6 carbon atoms or phenyl;
a pyrrolyl which may be substituted with alkyl having 1 to 4 carbon atoms;
a phenyl substituted with amino, alkoxy having 1 to 4 carbon atoms, pyrazolyl, isoxazolyl or morpholino;
a phenyl substituted with thiomorpholino which may be substituted with oxo;
a piperazino which may be substituted with alkyl having 1 to 4 carbon atoms or cyclohexyl;
a thiomorpholino which may be substituted with one or two oxos;
an amino which may be substituted with one or two alkyls having 1 to 4 carbon atoms; or
any one of substituents selected from guanidino, benzoimidazolyl, indazolyl, pyrazolyl, triazolyl, pyridyl, pyrrolidinyl, piperidino, hexamethyleneimino, morpholino, and cyclohexylamino; and
$R_2$ stands for a hydrogen, a cyano or an alkyl having 1 to 4 carbon atoms, with proviso that in a case of n=0, $R_1$ stands for a substituent other than a phenyl substituted with morpholino; in a case of n=1, $R_1$ stands for a substituent other than a pyridyl; in a case where $R_1$ is a morpholino and $R_2$ is a hydrogen, when either one of $X_1$ and $X_2$ is a hydrogen, the other stands for a substituent other than a fluorine.
(2) The compound or a pharmaceutically acceptable salt thereof according to the above (1), wherein $R_2$ is a hydrogen.
(3) The compound or a pharmaceutically acceptable salt thereof according to the above (2), wherein either one of $X_1$ and $X_2$ is a hydrogen, and the other is a fluorine.
(4) The compound or a pharmaceutically acceptable salt thereof according to the above (3), wherein $R_1$ is an imidazolyl which may be substituted with alkyl having 1 to 6 carbon atoms or phenyl.
(5) The compound or a pharmaceutically acceptable salt thereof according to the above (3), wherein $R_1$ is a pyrrolyl which may be substituted with alkyl having 1 to 4 carbon atoms.
(6) The compound or a pharmaceutically acceptable salt thereof according to the above (3), wherein $R_1$ is a phenyl substituted with amino, alkoxy having 1 to 4 carbon atoms, pyrazolyl, isoxazolyl, or morpholino.
(7) The compound or a pharmaceutically acceptable salt thereof according to the above (3), wherein $R_1$ is a phenyl substituted with thiomorpholino which may be substituted with oxo.
(8) The compound or a pharmaceutically acceptable salt thereof according to the above (3), wherein $R_1$ is a piperazino which may be substituted with alkyl having 1 to 4 carbon atoms or cyclohexyl.
(9) The compound or a pharmaceutically acceptable salt thereof according to the above (3), wherein $R_1$ is a thiomorpholino which may be substituted with one or two oxos.
(10) The compound or a pharmaceutically acceptable salt thereof according to the above (3), wherein $R_1$ is an amino which may be substituted with one or two alkyls having 1 to 4 carbon atoms.
(11) The compound or a pharmaceutically acceptable salt thereof according to the above (3), wherein $R_1$ is any one of substituents selected from guanidino, benzoimidazolyl, indazolyl, pyrazolyl, triazolyl, pyridyl, pyrrolidinyl, piperidino, hexamethyleneimino, morpholino, and cyclohexylamino.

(12) The compound or a pharmaceutically acceptable salt thereof according to the above (11), wherein $R_1$ is any one of substituents selected from pyrazolyl, triazolyl, piperidino, and morpholino.

(13) A pharmaceutical agent containing, as an active ingredient, at least one member of a compound and a pharmaceutically acceptable salt thereof, wherein the compound is represented by the following general formula (I):

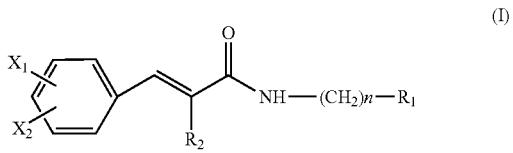

wherein n stands for an integer of from 0 to 4;

$X_1$ and $X_2$, which are identical or different, stand for a hydrogen, a fluorine, a trifluoromethyl, or a carboxy, and either one of $X_1$ and $X_2$ stands for a substituent other than a hydrogen;

$R_1$ stands for:
an imidazolyl which may be substituted with alkyl having 1 to 6 carbon atoms or phenyl;
a pyrrolyl which may be substituted with alkyl having 1 to 4 carbon atoms;
a phenyl substituted with amino, alkoxy having 1 to 4 carbon atoms, pyrazolyl, isoxazolyl or morpholino;
a phenyl substituted with thiomorpholino which may be substituted with oxo;
a piperazino which may be substituted with alkyl having 1 to 4 carbon atoms or cyclohexyl;
a thiomorpholino which may be substituted with one or two oxos;
an amino which may be substituted with one or two alkyls having 1 to 4 carbon atoms; or
any one of substituents selected from carboxy, guanidino, indolyl, benzoimidazolyl, indazolyl, pyrazolyl, triazolyl, pyridyl, pyrrolidinyl, piperidino, hexamethyleneimino, morpholino, and cyclohexylamino; and $R_2$ stands for a hydrogen, a cyano or an alkyl having 1 to 4 carbon atoms.

(14) The pharmaceutical agent according to the above (13), which is an analgesic.

(15) The pharmaceutical agent according to the above (14), wherein the analgesic is a therapeutic agent for chronic pains.

(16) The pharmaceutical agent according to the above (15), wherein the therapeutic agent for chronic pains is a therapeutic agent for lumbago, arthralgia, or neuropathic pains.

(17) The pharmaceutical agent according to the above (14), wherein the analgesic is a therapeutic agent for neuropathic pains.

(18) The pharmaceutical agent according to any one of the above (13) to (17), which is an oral preparation.

(19) The pharmaceutical agent according to any one of the above (13) to (17), which is an injectable preparation.

(20) A method of treating a pain disease, including administering an effective amount of at least one member of a compound represented by the general formula (I) and a pharmaceutically acceptable salt thereof as defined in the above (13) to a patient in need thereof.

(21) The method of treating a pain disease according to the above (20), wherein the pain disease is a chronic pain disease.

(22) The method of treating a pain disease according to the above (21), wherein the chronic pain disease is lumbago, arthralgia, or a neuropathic pain disease.

(23) The method of treating a pain disease according to the above (20), wherein the pain disease is a neuropathic pain.

(24) The method of treating a pain disease according to any one of the above (20) to (23), including administering with an oral preparation.

(25) The method of treating a pain disease according to any one of the above (20) to (23), including administering with an injectable preparation.

(26) Use of a compound represented by the following general formula (I) or a pharmaceutically acceptable salt thereof as defined in the above (13), in the manufacture of a pharmaceutical agent for the treatment of a pain disease.

(27) The use according to the above (26), wherein the pain disease is a chronic pain disease.

(28) The use according to the above (27), wherein the chronic pain disease is lumbago, arthralgia, or a neuropathic pain disease.

(29) The use according to the above (26), wherein the pain disease is a neuropathic pain.

(30) The use according to any one of the above (26) to (29), wherein the pharmaceutical agent is an oral preparation.

(31) The use according to any one of the above (26) to (29), wherein the pharmaceutical agent is an injectable preparation.

(32) A compound represented by the following general formula (I) or a pharmaceutically acceptable salt thereof as defined in the above (13), for use in the treatment of a pain disease.

(33) The compound or a pharmaceutically acceptable salt thereof according to the above (32), wherein the pain disease is a chronic pain disease.

(34) The compound or a pharmaceutically acceptable salt thereof according to the above (33), wherein the chronic pain disease is lumbago, arthralgia, or a neuropathic pain disease.

(35) The compound or a pharmaceutically acceptable salt thereof according to the above (33), wherein the pain disease is a neuropathic pain.

(36) The compound or a pharmaceutically acceptable salt thereof according to any one of the above (32) to (35), for use in an oral preparation.

(37) The compound or a pharmaceutically acceptable salt thereof according to any one of the above (32) to (35), for use in an injectable preparation.

The compound of the present invention can be combined with various pharmaceutical additives such as an excipient, a binder, a wetting agent, a disintegrant, a lubricant, or a diluent suitable for the dosage form to form a pharmaceutical composition. As the oral preparation, the compound can be prepared into a dosage form such as a tablet, a capsule, a powder, a granule, a liquid, a syrup, or a sublingual preparation. As the parenteral preparation, the compound can be formed into a preparation, such as injectable preparations for subcutaneous, intramuscular, articular cavity, or intravenous administration, suppositories for intrarectal administration, and inhalants for intranasal administration. In the formulation, the compound of the present invention may be used in the form of a pharmaceutically acceptable salt thereof, and the compounds can be used alone or in a proper combination. Further, the compound may be made into a combination drug with another pharmaceutically active ingredient.

As the additives when formed into an oral preparation, for example, a conventional excipient such as lactose, mannitol, corn starch or potato starch, a binder such as a crystalline cellulose, a cellulose derivative, gum arabic, corn starch, or gelatin, a disintegrant such as corn starch, potato starch, or carboxymethyl cellulose potassium, a lubricant such as talc or magnesium stearate, other additives such as a filler, a wetting agent, a buffer, a preservative, or a fragrance or the like can be properly combined, and a flavoring substance, an aromatizing agent or the like may be added thereto.

When prepared into a liquid preparation or an emulsive or suspending injectable preparation, a dissolution aid, a suspension agent, an emulsifier, a stabilizer, a preservative, an isotonic agent or the like which is ordinarily used may be properly added thereto, and the mixture is usually subjected to a sterile treatment.

The desired dose of the compound in the present invention may vary depending upon the subjects to be administered (age, body weight etc. of patients), the kinds or extent of the disease, the dosage form, the administration method, the administration period, and the like. In order to obtain a desired effect, the compound of the present invention can be orally administered usually in an amount of from 0.5 to 1000 mg, preferably from 1 to 500 mg, for adult at once or in several divided administrations per day. In the case of the parenteral administration, the daily dose is preferably from one-third to one-tenth of the dose level for each of the doses mentioned above, and the agent can be administered usually at once or in several divided administrations per day. In the case of a sustained-release preparation where a drug is released over a highly extended period of time, it is preferable that the administration is made once or so in a period of from one week to one year.

EXAMPLES

Next, the present invention will be hereinafter explained more specifically by means of Examples, without intending to limit the present invention to these Examples.

A melting point was determined using Yamato Scientific, Model MP-21, a melting point measuring instrument. No compensation of the thermometer was made. Nuclear magnetic resonance spectrum ($^1$H-NMR) was measured with Bruker, Model ARX-500, a nuclear magnetic resonance analyzer using TMS ($\delta$=0) as an internal standard substance. Silica gel column chromatography was performed using silica gel PSQ100B for normal phase chromatography (FUJI SILYSIA CHEMICAL LTD.). Thin-layer chromatography was performed using Silica gel F254 (Merck, No. 5715), and detection was made using a UV lamp and a 5% phosphomolybdic acid-ethanol color development reagent. Commercial products themselves were used as the reagents and solvents.

Example 1

Production of (E)-3-(2-Fluorophenyl)-N-[2-(1H-indol-3-yl)ethyl]-2-propenamide (Compound 1)

WSC.HCl (4.3 g, 22 mmol) was added to a methylene chloride (150 mL) solution of 2-fluorocinnamic acid (3.4 g, 21 mmol) and tryptamine (3.0 g, 19 mmol) at 0° C., and the mixture was stirred for 4 hours. DMF (120 mL) was added thereto, and the mixture was stirred in that state for 72 hours. The reaction solution was concentrated to ½ of the volume under a reduced pressure, and thereafter poured into an ice water, and the mixture was extracted with ethyl acetate. An organic layer was dried over anhydrous sodium sulfate. Thereafter, the residue obtained by distilling off the solvents under a reduced pressure was purified with silica gel column chromatography (n-hexane:ethyl acetate=1:1), to give the captioned compound (2.1 g, 51%) as an amorphous solid.

Example 2

Production of (E)-3-(2-Fluorophenyl)-N-(3-pyridylmethyl)-2-propenamide (Compound 2)

3-Aminomethylpyridine (2.0 g, 19 mmol) and WSC.HCl (3.8 g, 20 mmol) were added to a methylene chloride (60 mL) suspension of 2-fluorocinnamic acid (3.0 g, 18 mmol) at 0° C., and the mixture was stirred at room temperature for 3 hours. The reaction mixture was washed with water, and an organic layer was then dried over anhydrous sodium sulfate. The residue obtained by distilling off the solvents under a reduced pressure was purified with silica gel column chromatography (n-hexane:ethyl acetate=1:1), to give the captioned compound (3.9 g, 85%) as crystals.

Compounds 3 to 5 were produced in the same manner as this compound from appropriate starting compounds.

Example 3

Production of 2-[2-(4-Cyclohexylpiperazin-1-yl)ethyl]isoindole-1,3-dione

N-(2-Bromoethyl)phthalimide (2.5 g, 10 mmol) and potassium carbonate (2.0 g, 15 mmol) were added to a DMF (30 mL) solution of 1-cyclohexylpiperazine (1.7 g, 10 mmol) at room temperature, and the mixture was stirred at 100° C. for 24 hours. The reaction mixture was extracted with ethyl acetate, and an organic layer was washed with a saturated sodium chloride solution, and thereafter dried over anhydrous sodium sulfate. The residue obtained by distilling off the solvents under a reduced pressure was purified with silica gel column chromatography (n-hexane:ethyl acetate=7:3), to give the captioned compound (2.8 g, 82%) as an amorphous solid. $^1$H-NMR (DMSO-d$_6$) $\delta$: 1.38-1.41 (m, 11H), 2.35-2.37 (m, 4H), 2.54 (t, J=6.5 Hz, 2H), 3.21-3.22 (m, 4H), 3.70 (t, J=6.5 Hz, 2H), 7.83-7.89 (m, 4H).

Example 4

Production of 2-(4-Cyclohexylpiperazin-1-yl)ethylamine

Hydrazine monohydrate (0.8 g, 16 mmol) was added to an ethanol (30 mL) solution of the compound obtained in Example 3 (2.8 g, 8.2 mmol) at room temperature, and the mixture was heated under refluxing for 24 hours. The precipitated crystals were filtered away, and the solvent of the filtrate was distilled off under a reduced pressure. The residue was purified with silica gel column chromatography (chloroform:methanol=95:5), to give the captioned compound (1.3 g, 75%) as an oily product. $^1$H-NMR (DMSO-d$_6$) $\delta$: 1.05-1.17 (m, 5H), 1.53-1.55 (m, 1H), 1.68-1.71 (m, 4H), 2.11-2.13 (m, 1H), 2.30-2.45 (m 7H), 2.48-2.51 (m, 3H), 3.67 (t, J=6.6 Hz, 2H).

Example 5

Production of (E)-N-[2-(4-Cyclohexylpiperazin-1-yl)ethyl]-3-(2-fluorophenyl)-2-propenamide (Compound 6)

The same procedures as those in Compound 2 were carried out from 2-fluorocinnamic acid (1.3 g, 7.8 mmol), the compound obtained in Example 4 (1.8 g, 8.5 mmol), WSC.HCl (1.9 g, 10 mmol), and methylene chloride (50 mL), to give the captioned compound (1.9 g, 63%) as crystals.

Example 6

Production of 2-[3-(4-Cyclohexylpiperazin-1-yl)propyl]isoindole-1,3-dione

The same procedures as in Example 3 were carried out from 1-cyclohexylpiperazine (1.7 g, 10 mmol), N-(3-bromopropyl)phthalimide (2.7 g, 10 mmol), potassium carbonate (2.0 g, 15 mmol) and DMF (30 mL), to give the captioned compound (2.5 g, 71%) as an amorphous solid. $^1$H-NMR (DMSO-$d_6$) δ: 0.99-1.04 (m, 3H), 1.08-1.19 (m, 2H), 1.52-1.54 (m, 3H), 1.65-1.73 (m, 4H), 1.99-2.02 (m, 1H), 2.05-2.29 (m, 10H), 3.64 (t, J=6.6 Hz, 2H), 7.81-7.87 (m, 4H).

Example 7

Production of 3-(4-Cyclohexylpiperazin-1-yl)propylamine

The same procedures as in Example 4 were carried out from the compound obtained in Example 6 (2.5 g, 7.0 mmol), hydrazine monohydrate (0.5 g, 10 mmol), and ethanol (30 mL), to give the captioned compound as an oily product. This compound was used in the subsequent reaction without purification.

Example 8

Production of (E)-N-[3-(4-Cyclohexylpiperazin-1-yl)propyl]-3-(2-fluorophenyl)-2-propenamide (Compound 7)

The same procedures as those in Compound 2 were carried out from 2-fluorocinnamic acid (1.2 g, 7.2 mmol), the compound obtained in Example 7 (1.6 g, 7.1 mmol), WSC.HCl (1.6 g, 8.3 mmol), and methylene chloride (40 mL), to give the captioned compound (1.8 g, 69%) as crystals.

Example 9

Production of 2-(1-Methyl-1H-pyrrol-2-yl)ethanol

A THF (200 mL) solution of methyl 1-methylpyrrole-2-acetate (23 g, 150 mmol) was added dropwise to an ethanol solution (200 mL) of sodium borohydride (6.8 g, 180 mmol) and lithium chloride (7.6 g, 180 mmol) at room temperature, and the mixture was stirred in that state for 24 hours. The precipitated crystals were filtered away. Thereafter, the residue obtained by distilling off the filtrate under a reduced pressure was purified with silica gel column chromatography (n-hexane:ethyl acetate=1:1), to give the captioned compound (15.4 g, 93%) as an oily product. $^1$H-NMR (DMSO-$d_6$) δ: 2.66 (t, J=7.3 Hz, 2H), 3.49 (s, 3H), 3.54-3.58 (m, 2H), 4.66 (t, J=5.4 Hz, 1H), 5.75-5.76 (m, 1H), 5.83-5.84 (m, 1H), 6.56-6.67 (m, 1H).

Example 10

Production of 2-(1-Methyl-1H-pyrrol-2-yl)ethylmethanesulfonate

A methylene chloride (50 mL) solution of methanesulfonyl chloride (5.7 mL, 74 mmol) was added dropwise to a methylene chloride (80 mL) solution of the compound obtained in Example 9 (7.5 g, 67 mmol) and triethylamine (10 mL, 74 mmol) at room temperature, and the mixture was stirred in that state for 18 hours. The reaction mixture was washed with a saturated sodium chloride solution, and an organic layer was then dried over anhydrous sodium sulfate. The residue obtained by distilling off the solvents under a reduced pressure was purified with silica gel column chromatography (n-hexane:ethyl acetate=3:2), to give the captioned compound (4.5 g, 33%) as an oily product. $^1$H-NMR (DMSO-$d_6$) δ: 2.96 (t, J=6.9 Hz, 2H), 3.12 (s, 3H), 3.52 (s, 3H), 4.35 (t, J=6.9 Hz, 2H), 5.87-5.90 (m, 2H), 6.63-6.64 (m, 1H).

Example 11

Production of 2-[2-(1-Methyl-1H-pyrrol-2-yl)ethyl]isoindole-1,3-dione

The same procedures as in Example 3 were carried out from the compound obtained in Example 10 (4.5 g, 22 mmol), potassium phthalimide (4.7 g, 25 mmol), potassium carbonate (4.0 g, 29 mmol), and DMF (80 mL), to give the captioned compound (3.7 g, 66%) as an amorphous solid. $^1$H-NMR (DMSO-$d_6$) δ: 2.87 (t, J=7.4 Hz, 2H), 3.56 (s, 3H), 3.76 (t, J=7.4 Hz, 2H), 5.71-5.73 (m, 1H), 5.79-5.80 (m, 1H), 6.60-6.61 (m, 1H), 7.82-7.87 (m, 4H).

Example 12

Production of 2-(1-Methyl-1H-pyrrol-2-yl)ethylamine

The same treatments as in Example 4 were carried out from the compound obtained in Example 11 (3.7 g, 14 mmol), hydrazine monohydrate (1.0 mL, 21 mmol) and ethanol (160 mL), to give the captioned compound as an oily product. This compound was used in the subsequent reaction without purification.

Example 13

Production of (E)-3-(2-Fluorophenyl)-N-[2-(1-methyl-1H-pyrrol-2-yl)ethyl]-2-propenamide (Compound 8)

The same procedures as those in Compound 2 were carried out from 2-fluorocinnamic acid (3.0 g, 18 mmol), the compound obtained in Example 12 (1.5 g, 12 mmol), WSC.HCl (3.5 g, 18 mmol), and methylene chloride (60 mL), to give the captioned compound (1.8 g, 56%) as crystals.

Example 14

Production of (E)-3-(2-Fluorophenyl)-N-[2-(2-pyridyl)ethyl]-2-propenamide hydrochloride (Compound 9)

2-(2-Aminoethyl)pyridine (2.3 g, 19 mmol) and WSC.HCl (3.8 g, 20 mmol) were added to a methylene chloride (50 mL) suspension of 2-fluorocinnamic acid (3.0 g, 18 mmol) at 0° C., and the mixture was stirred at room temperature for 3 hours. The reaction mixture was washed with water, and an organic layer was then dried over anhydrous sodium sulfate. The residue obtained by distilling off the solvents under a reduced pressure was purified with silica gel column chromatography (n-hexane:ethyl acetate=1:1). A 4 mol/L hydrogen chloride-dioxane solution (13 mL, equivalent to HCl 52 mmol) was added dropwise to a methylene chloride (10 mL) solution of the purified product at room temperature. The mixture was stirred in that state for 1 hour. Thereafter, a petroleum ether was added to the residue obtained by distilling off the solvents under a reduced pressure, and the precipitated crystals were collected by filtration, to give the captioned compound (4.0 g, 73%).

Compounds 10 to 14 were produced in the same manner as this compound from appropriate starting compounds.

Example 15

Production of 2-[3-(4-Methylpiperazin-1-yl)propyl]isoindole-1,3-dione

The same procedures as in Example 3 were carried out from 1-methylpiperazine (1.9 g, 10 mmol), N-(3-bromopropyl)phthalimide (2.7 g, 10 mmol), potassium carbonate (2.0 g, 15 mmol) and DMF (30 mL), to give the captioned compound (2.6 g, 70%) as an amorphous solid. $^1$H-NMR (DMSO-$d_6$) δ: 1.70-1.75 (m, 2H), 1.90-2.30 (m, 13H), 3.63 (t, J=6.7 Hz, 2H), 7.82-7.87 (m, 4H).

Example 16

Production of 3-(4-Methylpiperazin-1-yl)propylamine

The same procedures as in Example 4 were carried out from the compound obtained in Example 15 (1.1 g, 3.8 mmol), hydrazine monohydrate (0.4 g, 8.0 mmol) and ethanol (30 mL), to give the captioned compound (0.3 g, 48%) as an oily product. $^1$H-NMR (DMSO-$d_6$) δ: 1.43-1.49 (m, 2H), 2.13 (s, 3H), 2.20-2.40 (br, 9H), 2.49-2.54 (m, 3H).

Example 17

Production of (E)-3-(2-Fluorophenyl)-N-[3-(4-methylpiperazin-1-yl)propyl]-2-propenamide dihydrochloride (Compound 15)

The same procedures as those in Compound 9 were carried out from 2-fluorocinnamic acid (0.39 g, 1.5 mmol), the compound obtained in Example 16 (0.24 g, 1.5 mmol), WSC.HCl (0.29 g, 1.5 mmol), and methylene chloride (4 mL), to give the captioned compound (0.11 g, 22%) as crystals.

Example 18

Production of tert-Butyl 4-[2-(1,3-dioxo-1,3-dihydroisoindol-2-yl)ethyl]piperazine-1-carboxylate The same procedures as in Example 3 were carried out from 1-(tert-butoxycarbonyl)piperazine (1.9 g, 10 mmol), N-(2-bromoethyl)phthalimide (2.5 g, 10 mmol), potassium carbonate (2.0 g, 15 mmol) and DMF (30 mL), to give the captioned compound (1.8 g, 69%) as an amorphous solid. $^1$H-NMR (DMSO-$d_6$) δ: 1.38 (s, 9H), 2.36-2.37 (m, 4H), 2.54 (t, J=6.5 Hz, 2H), 3.20-3.22 (m, 4H), 3.70 (t, J=6.5 Hz, 2H), 7.83-7.89 (m, 4H).

Example 19

Production of tert-Butyl 4-(2-aminoethyl)piperazine-1-carboxylate

The same procedures as in Example 4 were carried out from the compound obtained in Example 18 (1.8 g, 5.0 mmol), hydrazine monohydrate (0.5 g, 10 mmol) and ethanol (30 mL), to give the captioned compound (0.8 g, 72%) as an oily product. $^1$H-NMR (DMSO-$d_6$) δ: 1.39 (s, 9H), 2.29-2.35 (m, 8H), 2.67 (t, J=6.6 Hz, 2H), 3.28-3.30 (m, 2H).

Example 20

Production of (E)-3-(2-Fluorophenyl)-N-[2-(piperazin-1-yl)ethyl]-2-propenamide dihydrochloride (Compound 16)

The same procedures as those in Compound 9 were carried out from 2-fluorocinnamic acid (0.34 g, 2.0 mmol), the compound obtained in Example 19 (0.55 g, 2.1 mmol), WSC.HCl (0.42 g, 2.2 mmol), and methylene chloride (20 mL), to give the captioned compound (0.4 g, 63%) as crystals.

Example 21

Production of tert-Butyl 4-[3-(1,3-dioxo-1,3-dihydroisoindol-2-yl)propyl]piperazine-1-carboxylate The same procedures as in Example 3 were carried out from 1-(tert-butoxycarbonyl)piperazine (1.0 g, 10 mmol), N-(3-bromopropyl)phthalimide (2.7 g, 10 mmol), potassium carbonate (2.0 g, 15 mmol), and DMF (30 mL), to give the captioned compound (1.1 g, 38%) as an amorphous solid. $^1$H-NMR (DMSO-$d_6$) δ: 1.36 (s, 9H), 1.72-1.76 (m, 2H), 2.20-2.22 (m, 4H), 2.32 (t, J=6.7 Hz, 2H), 3.33-3.35 (m, 4H), 3.64 (t, J=6.9 Hz, 2H), 7.82-7.88 (m, 4H).

Example 22

Production of tert-Butyl 4-(3-aminopropyl)piperazine-1-carboxylate

The same procedures as in Example 4 were carried out from the compound obtained in Example 21 (4.7 g, 13 mmol), hydrazine monohydrate (0.7 g, 14 mmol) and ethanol (80 mL), to give the captioned compound (2.6 g, 87%) as an oily product. $^1$H-NMR (DMSO-$d_6$) δ: 1.39 (s, 9H), 1.73-1.75 (m, 2H), 2.29-2.35 (m, 8H), 2.68 (t, J=6.8 Hz, 2H), 3.28-3.30 (m, 2H).

Example 23

Production of (E)-3-(2-Fluorophenyl)-N-[3-(piperazin-1-yl)propyl]-2-propenamide dihydrochloride (Compound 17)

The same procedures as those in Compound 9 were carried out from 2-fluorocinnamic acid (2.6 g, 16 mmol), the compound obtained in Example 22 (4.0 g, 16 mmol), WSC.HCl (3.5 g, 18 mmol), and methylene chloride (80 mL), to give the captioned compound (2.6 g, 50%) as crystals.

Example 24

Production of (E)-3-(2-Fluorophenyl)-2-propenoyl chloride

Thionyl chloride (55 mL, 0.75 mol) was added to 2-fluorocinnamic acid (25.0 g, 0.15 mol), and the mixture was heated under refluxing for 2 hours. The solvent was distilled off under a reduced pressure, to give the captioned compound (27.8 g, quant) as an oily product. $^1$H-NMR (CDCl$_3$) δ: 6.75 (d, J=15.8 Hz, 1H), 7.13-7.17 (m, 1H), 7.21-7.24 (m, 1H), 7.44-7.47 (m, 1H), 7.54-7.58 (m, 1H), 7.94 (d, J=15.8 Hz, 1H).

Example 25

Production of (2,5-Dioxopyrrolidin-1-yl) (E)-3-(2-fluorophenyl)-2-propenoate A methylene chloride (200 mL) solution of the compound obtained in Example 24 (27.8 g, 0.15 mol) was added dropwise to a methylene chloride (200 mL) solution of HOSu (17.3 g, 0.15 mol) and triethylamine (23 mL, 0.17 mol) at 0° C. The mixture was stirred at room temperature for 19 hours, the reaction mixture was then washed with water, and an organic layer was dried over anhydrous sodium sulfate in the presence of a small amount of silica gel. The precipitated crystals obtained by distilling off the solvent under a reduced pressure were filtered with diethyl ether, to give crude crystals (33.6 g). The crude crystals (33.6 g) were recrystallized from ethyl acetate (210 mL), to give the captioned compound (27.5 g, 70%). Mp. 148-149° C. $^1$H-NMR (DMSO-d$_6$) δ: 2.88 (s, 4H), 7.03 (d, J=16.2 Hz, 1H), 7.32-7.38 (m, 2H), 7.58-7.62 (m, 1H), 7.98-8.04 (m, 2H).

Example 26

Production of (E)-3-(2-Fluorophenyl)-N-[2-(1H-imidazol-4-yl)ethyl]-2-propenamide (Compound 18)

Sodium hydrogencarbonate (4.2 g, 50 mmol) was added to an aqueous solution (50 mL) of 2-imidazol-4-ylethylamine (4.7 g, 18 mmol) at room temperature. The mixture was stirred in that state for 30 minutes, a dioxane (60 mL) solution of the compound obtained in Example 25 (4.7 g, 18 mmol) was then added dropwise thereto, and the mixture was stirred at room temperature for 18 hours. The reaction mixture was extracted with ethyl acetate, and an organic layer was washed with a saturated sodium chloride solution, and then dried over anhydrous sodium sulfate. The residue obtained by distilling off the solvents under a reduced pressure was purified with silica gel column chromatography (chloroform:methanol=4:1), to give the captioned compound (1.7 g, 36%) as crystals.

Compound 19 was produced in the same manner as this compound from an appropriate starting compound.

Example 27

Production of 2-[2-(4-Methylpiperazin-1-yl)ethyl]isoindole-1,3-dione

The same procedures as in Example 3 were carried out from 1-methylpiperazine (1.0 g, 10 mmol), N-(2-bromoethyl)phthalimide (2.5 g, 10 mmol), potassium carbonate (2.0 g, 15 mmol) and DMF (30 mL), to give the captioned compound (1.6 g, 59%) as an amorphous solid. $^1$H-NMR (DMSO-d$_6$) δ: 2.09 (s, 3H), 2.10-2.40 (m, 8H), 2.51 (t, J=6.5 Hz, 2H), 3.68 (t, J=6.5 Hz, 2H), 7.83-7.89 (m, 4H).

Example 28

Production of 2-(4-Methylpiperazin-1-yl)ethylamine

The same procedures as in Example 4 were carried out from the compound obtained in Example 27 (1.6 g, 5.9 mmol), hydrazine monohydrate (0.6 g, 12 mmol) and ethanol (30 mL), to give the captioned compound as an oily product. This compound was used in the subsequent reaction without purification.

Example 29

Production of (E)-3-(2-Fluorophenyl)-N-[2-(4-methylpiperazin-1-yl)ethyl]-2-propenamide (Compound 20)

The same procedures as those in Compound 18 were carried out from the compound obtained in Example 28 (0.21 g, 1.5 mmol), the compound obtained in Example 25 (0.39 g, 1.5 mmol), sodium hydrogencarbonate (0.17 g, 2.0 mmol), water (5 mL), and dioxane (5 mL), to give the captioned compound (0.15 g, 34%) as crystals.

Example 30

Production of 2-(2-Imidazol-1-ylethyl)isoindoline 1,3-dione

A toluene (400 mL) solution of imidazole (20 g, 0.29 mol) and N-(2-bromoethyl)phthalimide (33 g, 0.13 mol) was heated under refluxing for 16 hours. Chloroform was added to the residue obtained by distilling off the solvent under a reduced pressure, and the mixture was washed with a saturated aqueous sodium hydrogencarbonate solution and a saturated sodium chloride solution. An organic layer was dried over anhydrous sodium sulfate, and diethyl ether was then added to the residue obtained by distilling off the solvents under a reduced pressure. The precipitated crystals were collected by filtration, to give the captioned compound (20 g, 64%). Mp. 155-156° C. $^1$H-NMR (DMSO-d$_6$) δ: 3.92 (t, J=6.1 Hz, 2H), 4.25 (t, J=6.1 Hz, 2H), 6.81 (s, 1H), 7.13 (s, 1H), 7.34 (s, 1H), 7.83-7.85 (m, 4H).

Example 31

Production of 2-Imidazol-1-ylethylamine

The same treatments as in Example 4 were carried out from the compound obtained in Example 30 (2.2 g, 9.1 mmol), hydrazine monohydrate (0.7 g, 14 mmol) and ethanol (40 mL), to give the captioned compound as an oily product. This compound was used in the subsequent reaction without purification.

Example 32

Production of (E)-3-(2-Fluorophenyl)-N-[2-imidazol-1-ethyl]-2-propenamide hydrochloride (Compound 21)

A methylene chloride (30 mL) solution of the compound obtained in Example 25 (2.6 g, 10 mmol) was added to a methylene chloride (20 mL) solution of the compound obtained in Example 31 (0.66 g, 5.9 mmol) at room temperature, and the mixture was stirred in that state for 5 hours. The reaction mixture was washed with water, and an organic layer was then dried over anhydrous sodium sulfate. The residue obtained by distilling off the solvents under a reduced pressure was purified with silica gel column chromatography (n-hexane:ethyl acetate=3:2). A 4 mol/L hydrogen chloride-dioxane solution (8 mL, equivalent to HCl 32.0 mmol) was added dropwise to a methylene chloride (10 mL) solution of the purified product at room temperature. The mixture was stirred in that state for 1 hour, and a petroleum ether was then added to the residue obtained by distilling off the solvents under a reduced pressure, to give the captioned compound (1.3 g, 50%) as an amorphous solid.

Example 33

Production of 2-[2-(Benzimidazol-1-yl)ethyl]isoindole-1,3-dione

N-(2-Bromoethyl)phthalimide (7.6 g, 30 mmol) and anhydrous potassium carbonate (6.2 g, 45 mmol) were added to a DMF (150 mL) solution of benzimidazole (4.7 g, 40 mmol) at room temperature, and the mixture was stirred at 100° C. for 18 hours. Water was added to the reaction mixture, the mixture was extracted with ethyl acetate, and an organic layer was washed with a saturated sodium chloride solution, and then dried over anhydrous sodium sulfate. The solid obtained by distilling off the solvents under a reduced pressure was washed with diethyl ether, to give the captioned compound (2.6 g, 30%) as an amorphous solid. 1H-NMR (DMSO-$d_6$) δ: 3.98 (t, J=6.1 Hz, 2H), 4.52 (t, J=6.1 Hz, 2H), 7.15-7.18 (m, 2H), 7.53-7.61 (m, 2H), 7.81 (s, 4H), 8.17 (s, 1H).

Example 34

Production of (E)-N-[2-(Benzoimidazol-1-yl)ethyl]-3-(2-fluorophenyl)-2-propenamide (Compound 22)

Hydrazine monohydrate (0.8 g, 15 mmol) was added to an ethanol (100 mL) solution of the compound obtained in Example 33 (2.6 g, 8.9 mmol) at room temperature, and the mixture was heated under refluxing for 2 hours. The precipitated crystals were filtered away, and the solvent of the filtrate was then distilled off under a reduced pressure, to give 2-(benzoimidazol-1-yl)ethylamine as an oily product. This compound was used in the subsequent reaction without purification. This compound (1.1 g, 7.0 mmol) and WSC.HCl (2.3 g, 12 mmol) were added to a methylene chloride (80 mL) suspension of 2-fluorocinnamic acid (1.7 g, 10 mmol) at 0° C., and the mixture was stirred at room temperature for 1 hour. The reaction mixture was washed with water, and an organic layer was then dried over anhydrous sodium sulfate. The residue obtained by distilling off the solvents under a reduced pressure was purified with silica gel column chromatography (NH, n-hexane:ethyl acetate=1:1), to give the captioned compound (0.7 g, 33%).

Compounds 23 to 37 were produced in the same manner as this compound from appropriate starting compounds.

Example 35

Production of 2-[2-(Pyrazol-1-yl)ethyl]isoindole-1,3-dione

Pyrazole (2.0 g, 35 mmol) was added to a DMF (100 mL) solution of sodium hydride (60% dispersion in mineral oil) (1.4 g, 35 mmol) at 0° C., and the mixture was stirred at room temperature for 1 hour. A DMF (50 mL) solution of N-(bromoethyl)phthalamide (7.6 g, 30 mmol) was added dropwise to the reaction mixture at 0° C., and the mixture was stirred at room temperature for 18 hours. Water was added to the reaction mixture, the mixture was extracted with ethyl acetate, and an organic layer was washed with a saturated sodium chloride solution, and then dried over anhydrous sodium sulfate. The solid obtained by distilling off the solvents under a reduced pressure was washed with diethyl ether, to give the captioned compound (4.0 g, 56%) as an amorphous solid. 1H-NMR (DMSO-$d_6$) δ: 3.93 (t, J=5.8 Hz, 2H), 4.38 (t, J=5.8 Hz, 2H), 6.15 (s, 1H), 7.31 (s, 1H), 7.70 (s, 1H), 7.83-7.85 (m, 4H).

Example 36

Production of (E)-3-(2-Fluorophenyl)-N-[2-(pyrazol-1-yl)ethyl]-2-propenamide (Compound 38)

The same procedures as those in Compound 22 were carried out from the compound obtained in Example 35 (4.0 g, 17 mmol), hydrazine monohydrate (1.0 g, 20 mmol), and ethanol (200 mL), to give 2-(pyrazol-1-yl)ethylamine as an oily product. This compound was used in the subsequent reaction without purification. The same procedures as those in Compound 22 were carried out from 2-fluorocinnamic acid (0.7 g, 4.0 mmol), this compound (0.5 g, 4.0 mmol), WSC.HCl (1.0 g, 5.0 mmol), and methylene chloride (50 mL), to give the captioned compound (0.4 g, 9%) as crystals.

Example 37

Production of 2-[2-([1,2,4]triazol-1-yl)ethyl]isoindole-1,3-dione

The same procedures as in Example 33 were carried out from 1H-[1,2,4]triazole (2.0 g, 30 mmol), N-(2-bromoethyl)phthalimide (7.6 g, 30 mmol), anhydrous potassium carbonate (6.2 g, 45 mmol), and DMF (150 mL), to give the captioned compound (1.7 g, 23%) as an amorphous solid. 1H-NMR (DMSO-$d_6$) δ: 3.96 (t, J=5.9 Hz, 2H), 4.46 (t, J=5.9 Hz, 2H), 7.84-7.86 (m, 5H), 8.51 (s, 1H).

Example 38

Production of (E)-3-(2-Fluorophenyl)-N-[2-([1,2,4]triazol-1-yl)ethyl]-2-propenamide dihydrochloride (Compound 39)

The same procedures as those in Compound 22 were carried out from the compound obtained in Example 37 (1.5 g, 6.0 mmol), hydrazine monohydrate (0.5 g, 10 mmol), and ethanol (100 mL), to give 2-([1,2,4]triazol-1-yl)ethylamine as an oily product. This compound was used in the subsequent reaction without purification. The same procedures as those in Compound 22 were carried out from 2-fluorocinnamic acid (1.0 g, 6.0 mmol), this compound (0.6 g, 5.0 mmol), WSC.HCl (1.5 g, 8.0 mmol), and methylene chloride (70 mL), to give an oily product. The oily product was dissolved in methylene chloride (10 mL), and a 4 mol/L hydrogen chloride-dioxane solution (13 mL, equivalent to HCl 52 mmol) was added dropwise thereto at room temperature. The mixture was stirred in that state for 3 hours, and the solvents were distilled off under a reduced pressure, to give the captioned compound (0.4 g, 25%) as an amorphous solid.

Example 39

Production of 2-[2-([1,2,3]triazol-1-yl)ethyl]isoindole-1,3-dione

The same procedures as in Example 33 were carried out from 1H-[1,2,3]triazole (2.0 g, 30 mmol), N-(2-bromoethyl)phthalimide (7.6 g, 30 mmol), anhydrous potassium carbonate (6.2 g, 45 mmol), and DMF (150 mL), to give the captioned compound (3.3 g, 45%) as an amorphous solid. $^1$H-NMR (DMSO-$d_6$) δ: 3.99 (t, J=6.0 Hz, 2H), 4.70 (t, J=6.0 Hz, 2H), 7.70 (s, 2H), 7.84-7.85 (m, 4H).

Example 40

Production of (E)-3-(2-Fluorophenyl)-N-[2-([1,2,3]triazol-1-yl)ethyl]-2-propenamide (Compound 40)

The same procedures as those in Compound 22 were carried out from the compound obtained in Example 39 (3.0 g, 12 mmol), hydrazine monohydrate (0.9 g, 18 mmol), and ethanol (200 mL), to give 2-([1,2,3]triazol-1-yl)ethylamine as an oily product. This compound was used in the subsequent reaction without purification. The same procedures as those in Compound 22 were carried out from 2-fluorocinnamic acid (1.4 g, 9.0 mmol), this compound (0.9 g, 8.0 mmol), WSC.HCl (1.9 g, 10 mmol), and methylene chloride (70 mL), to give the captioned compound (0.4 g, 20%) as crystals.

Example 41

Production of 1-(2-Chloroethyl)-1H-indole

Sodium hydroxide (4.0 g, 100 mmol) was finely powdered in an argon atmosphere, and anhydrous 1,2-dichloroethane (60 mL), indole (3.5 g, 30 mmol) and tetra-n-butylammonium hydrogensulfate (0.7 g, 2.0 mmol) were then added thereto. The mixture was stirred at room temperature for 1 hour, and then stirred at 50° C. for 18 hours. The reaction mixture was washed with water, and an organic layer was washed with a saturated sodium chloride solution, and then dried over anhydrous sodium sulfate. The residue obtained by distilling off the solvents under a reduced pressure was purified with silica gel column chromatography (NH, n-hexane:ethyl acetate=7:3), to give the captioned compound (1.3 g, 24%) as an oily product. $^1$H-NMR (DMSO-$d_6$) δ: 3.96 (t, J=6.0 Hz, 2H), 4.52 (t, J=6.0 Hz, 2H), 6.45 (d, J=3.2 Hz, 1H), 7.02-7.05 (m, 1H), 7.12-7.15 (m, 1H), 7.40-7.41 (m, 1H), 7.50-7.56 (m, 2H).

Example 42

Production of 2-[2-(Indol-1-yl)ethyl]isoindole-1,3-dione

The same procedures as in Example 33 were carried out from the compound obtained in Example 41 (1.3 g, 7.2 mmol), potassium phthalimide (1.7 g, 9.0 mmol), and DMF (130 mL), to give the captioned compound (0.9 g, 43%) as an amorphous solid. $^1$H-NMR (DMSO-$d_6$) δ: 3.94 (t, J=6.3 Hz, 2H), 4.45 (t, J=6.3 Hz, 2H), 6.36 (s, 1H), 6.94-6.97 (m, 1H), 7.03-7.06 (m, 1H), 7.28 (s, 1H), 7.40-7.42 (m, 1H), 7.48-7.50 (m, 1H), 7.81 (s, 4H).

Example 43

Production of (E)-3-(2-Fluorophenyl)-N-[2-indol-1-yl)ethyl]-2-propenamide (Compound 41)

The same procedures as those in Compound 22 were carried out from the compound obtained in Example 42 (0.9 g, 3.0 mmol), hydrazine monohydrate (0.3 g, 6.0 mmol), and ethanol (50 mL), to give 2-(indol-1-yl)ethylamine as an oily product. This compound was used in the subsequent reaction without purification. The same procedures as those in Compound 22 were carried out from 2-fluorocinnamic acid (0.5 g, 3.0 mmol), this compound (0.3 g, 2.0 mmol), WSC.HCl (0.8 g, 4.0 mmol), and methylene chloride (30 mL), to give the captioned compound (0.4 g, 17%) as crystals.

Example 44

Production of 2-[2-(2-Methylimidazol-1-yl)ethyl]isoindole-1,3-dione

The same procedures as in Example 33 were carried out from 2-methylimidazole (3.3 g, 40 mmol), N-(2-bromoethyl)phthalimide (7.6 g, 30 mmol), anhydrous potassium carbonate (6.2 g, 45 mmol), and DMF (150 mL), to give the captioned compound (1.8 g, 23%) as an amorphous solid. $^1$H-NMR (DMSO-$d_6$) δ: 2.22 (s, 3H), 3.87 (t, J=6.2 Hz, 2H), 4.15 (t, J=6.2 Hz, 2H), 6.61 (s, 1H), 6.92 (s, 1H), 7.87 (m, 4H).

Example 45

Production of (E)-3-(2-Fluorophenyl)-N-[2-(2-methylimidazol-1-yl)ethyl]-2-propenamide (Compound 42)

The same procedures as those in Compound 22 were carried out from the compound obtained in Example 44 (1.7 g, 6.6 mmol), hydrazine monohydrate (0.5 g, 10 mmol), and ethanol (100 mL), to give 2-(2-methylimidazol-1-yl)ethanamine as an oily product. This compound was used in the subsequent reaction without purification. The same procedures as those in Compound 22 were carried out from 2-fluorocinnamic acid (0.8 g, 5.0 mmol), this compound (0.5 g, 4.0 mmol), WSC.HCl (1.3 g, 7.0 mmol), and methylene chloride (50 mL), to give the captioned compound (0.4 g, 32%) as crystals.

Example 46

Production of 1-(2-Chloroethyl)-2-phenyl-1H-imidazole

The same procedures as in Example 41 were carried out from 2-phenylimidazole (10.0 g, 69 mmol), sodium hydroxide (9.2 g, 213 mmol), tetra-n-butylammonium hydrogensulfate (1.6 g, 4.6 mmol), and 1,2-dichloroethane (140 mL), to give the captioned compound (5.4 g, 38%) as an oily product. $^1$H-NMR (DMSO-$d_6$) δ: 3.93 (t, J=6.0 Hz, 2H), 4.36 (t, J=6.0 Hz, 2H), 7.03 (s, 1H), 7.43-7.59 (m, 4H), 7.59-7.61 (m, 2H).

Example 47

Production of 2-[2-(2-Isopropylimidazol-1-yl)ethyl]isoindole-1,3-dione

N-(2-Bromoethyl)phthalimide (12.7 g, 50 mmol) and anhydrous potassium carbonate (6.9 g, 50 mmol) were added to a DMF (100 mL) solution of 2-isopropylimidazole (5.0 g, 45 mmol), and the mixture was stirred at 100° C. for 14 hours. The reaction mixture was poured into ice water, and extracted with ethyl acetate. An organic layer was dried over anhydrous sodium sulfate. Thereafter, the residue obtained by distilling off the solvents under a reduced pressure was purified with silica gel column chromatography (PSQ100B, chloroform:methanol=100:1), to give the captioned compound (2.8 g, 22%) as an oily product. $^1$H-NMR (DMSO-$d_6$) δ: 1.12 (d, J=6.7 Hz, 6H), 2.90-3.00 (m, 1H), 3.88 (t, J=6.3 Hz, 2H), 4.18 (t, J=6.3 Hz, 2H), 6.68 (s, 1H), 6.93 (s, 1H), 7.84-7.86 (m, 4H).

Example 48

Production of 2-(2-Isopropylimidazol-1-yl)ethylamine

Hydrazine monohydrate (0.9 mL, 19 mmol) was added to an ethanol (80 mL) solution of the compound obtained in Example 47 (2.7 g, 9.5 mmol), and the mixture was heated under refluxing for 6 hours. The reaction mixture was cooled to room temperature, and the precipitated crystals were filtered away. Methylene chloride was added to the residue obtained by distilling off the solvent of the filtrate under a reduced pressure, and insoluble substances were filtered away. The solvents of the filtrate were distilled off under a reduced pressure, to give the captioned compound (1.1 g, 77%) as an oily product. $^1$H-NMR (DMSO-$d_6$) δ: 1.18 (d, J=6.8 Hz, 6H), 2.79 (t, J=6.7 Hz, 2H), 3.04-3.07 (m, 1H), 3.83 (t, J=6.7 Hz, 2H), 6.73 (s, 1H), 6.99 (s, 1H).

Example 49

Production of (E)-3-(2-Fluorophenyl)-N-[2-(2-isopropylimidazol-1-yl)ethyl]-2-propenamide The same procedures as those in Compound 22 were carried out from 2-fluorocinnamic acid (1.1 g, 6.7 mmol), the compound obtained in Example 48 (1.1 g, 7.3 mmol), WSC.HCl (1.5 g, 8.0 mmol), and methylene chloride (80 mL), to give the captioned compound (1.3 g, 68%) as an oily product. $^1$H-NMR (DMSO-$d_6$) δ: 1.18 (d, J=6.7 Hz, 6H), 3.00-3.03 (m, 1H), 3.45-3.48 (m, 2H), 4.02 (t, J=6.3 Hz, 2H), 6.70 (d, J=15.9 Hz, 1H), 6.76 (d, J=0.7 Hz, 1H), 7.01 (d, J=0.7 Hz, 1H), 7.26-7.30 (m, 2H), 7.41-7.43 (m, 1H), 7.51 (d, J=15.9 Hz, 1H), 7.63-7.65 (m, 1H), 8.40 (s, 1H).

Example 50

Production of (E)-3-(2-Fluorophenyl)-N-[2-(2-isopropylimidazol-1-yl)ethyl]-2-propenamide hydrochloride (Compound 43)

A 4 mol/L hydrogen chloride-dioxane solution (3.3 mL, equivalent to HCl 13 mmol) was added dropwise to a methylene chloride (20 mL) solution of the compound obtained in Example 49 (1.3 g, 4.5 mmol) at room temperature. The mixture was stirred for 1 hour, and the solvents were then distilled off under a reduced pressure, to give the captioned compound (1.2 g, 83%) as an amorphous solid.

Example 51

Production of 2-[2-(2-Phenylimidazol-1-yl)ethyl]isoindole-1,3-dione

The same procedures as in Example 47 were carried out from the compound obtained in Example 46 (5.4 g, 26 mmol), potassium phthalimide (5.8 g, 31 mmol) and DMF (130 mL), to give the captioned compound (5.4 g, 66%) as an oily product. $^1$H-NMR (DMSO-$d_6$) δ: 3.76 (t, J=5.8 Hz, 2H), 4.39 (t, J=5.8 Hz, 2H), 6.93 (s, 1H), 7.18-7.24 (m, 3H), 7.29 (s, 1H), 7.33-7.35 (m, 2H), 7.70-7.72 (m, 2H), 7.79-7.80 (m, 2H).

Example 52

Production of 2-(2-Phenylimidazol-1-yl)ethylamine

The same procedures as in Example 48 were carried out from the compound obtained in Example 51 (5.4 g, 17 mmol), hydrazine monohydrate (1.7 mL, 34 mmol), and ethanol (150 mL), to give the captioned compound (3.1 g, 98%) as an oily product. $^1$H-NMR (DMSO-$d_6$) δ: 2.84 (t, J=6.7 Hz, 2H), 3.98 (t, J=6.7 Hz, 2H), 6.99 (s, 1H), 7.32 (s, 1H), 7.43-7.49 (m, 3H), 7.62-7.64 (m, 2H).

Example 53

Production of (E)-3-(2-Fluorophenyl)-N-[2-(2-phenylimidazol-1-yl)ethyl]-2-propenamide (Compound 44)

The same procedures as those in Compound 22 were carried out from 2-fluorocinnamic acid (2.8 g, 15 mmol), the compound obtained in Example 52 (3.1 g, 17 mmol), WSC.HCl (3.5 g, 18 mmol), and methylene chloride (100 mL), to give the captioned compound (4.0 g, 79%) as crystals.

Example 54

Production of 2-[3-(Imidazol-1-yl)propyl]isoindole-1,3-dione

The same procedures as in Example 33 were carried out from N-(3-bromopropyl)phthalimide (5.4 g, 20 mmol), imidazole (1.4 g, 20 mmol), anhydrous potassium carbonate (4.1 g, 30 mmol), and DMF (100 mL), to give the captioned compound (2.5 g, 49%) as an oily product. $^1$H-NMR (DMSO-$d_6$) δ: 2.01-2.07 (m, 2H), 3.56 (t, J=6.7 Hz, 2H), 4.02 (t, J=7.1 Hz, 2H), 6.87 (s, 1H), 7.19 (s, 1H), 7.63 (s, 1H), 7.83-7.88 (m, 4H).

Example 55

Production of (E)-3-(2-Fluorophenyl)-N-[3-(imidazol-1-yl)propyl]-2-propenamide hydrochloride (Compound 45)

The same procedures as those in Compound 22 were carried out from the compound obtained in Example 54 (2.5 g, 10 mmol), hydrazine monohydrate (1.0 g, 20 mmol), and ethanol (100 mL), to give 3-(imidazol-1-yl)propylamine as an oily product. This compound was used in the subsequent reaction without purification. The same procedures as those in Compound 22 were carried out from 2-fluorocinnamic acid (1.7 g, 10 mmol), this compound (1.2 g, 10 mmol), WSC.HCl (2.3 g, 12 mmol), and methylene chloride (120 mL), to give a free form as an oily product. A 4 mol/L hydrogen chloride-dioxane solution (3.0 mL, equivalent to HCl 12 mmol) was added dropwise to a methylene chloride (10 mL) solution of the free form at room temperature. The mixture was stirred in that state for 24 hours, and the solvents were distilled off under a reduced pressure, to give the captioned compound (0.8 g, 26%) as an oily product.

Example 56

Production of (E)-3-(4-Fluorophenyl)-2-methyl-2-propenoic acid

Methylmalonic acid (11.4 g, 97 mmol) and piperidine (9.6 mL, 97 mmol) were added to a pyridine (200 mL) solution of 4-fluorobenzaldehyde (8.0 g, 65 mmol), and the mixture was stirred at 100° C. for 16 hours. Water was added to the residue obtained by distilling off the solvent under a reduced pressure, the solution was made acidic with a diluted hydrochloric acid, and the precipitated crystals were collected by filtration. The crystals obtained were dissolved in diethyl ether, and the solution was back-extracted with a 10% aqueous sodium hydroxide solution. An aqueous layer was made acidic with a diluted hydrochloric acid, and the precipitated crystals were collected by filtration, to give the captioned compound (7.1 g, 61%). Mp. 154-155° C. $^1$H-NMR (DMSO-$d_6$) δ: 2.02 (s, 3H), 7.26-7.29 (m, 2H), 7.52-7.59 (m, 3H), 12.55 (s, 1H).

Example 57

Production of (E)-3-(4-Fluorophenyl)-2-methyl-N-(3-morpholinopropyl)-2-propenamide (Compound 46)

The same procedures as those in Compound 22 were carried out from the compound obtained in Example 56 (2.5 g, 14 mmol), 3-morpholinopropylamine (2.2 mL, 15 mmol), WSC.HCl (3.2 g, 17 mmol), and methylene chloride (100 mL), to give the captioned compound (2.6 g, 60%) as crystals.

Example 58

Production of Ethyl 2-formylbenzoate

The same procedures as in Example 47 were carried out from o-phthalaldehydic acid (20 g, 133 mmol), iodoethane (13 mL, 160 mmol), anhydrous potassium carbonate (22.1 g, 160 mmol), and DMF (200 mL), to give the captioned compound (20.9 g, 88%) as an oily product. $^1$H-NMR (DMSO-$d_6$) δ: 1.34 (t, J=7.0 Hz, 3H), 4.37 (q, J=7.0 Hz, 2H), 7.77-7.91 (m, 4H), 10.40 (s, 1H).

Example 59

Production of (E)-3-(2-Ethoxycarbonylphenyl)-2-propenoic acid

Malonic acid (18.3 g, 176 mmol) and piperidine (1.2 mL, 12 mmol) were added to a pyridine (400 mL) solution of the compound obtained in Example 58 (20.8 g, 117 mmol) at room temperature, and the mixture was heated under refluxing for 2 hours. Water was added to the residue obtained by distilling off the solvent under a reduced pressure, and the solution was made acidic with a diluted hydrochloric acid. The precipitated crystals were collected by filtration and washed with water, to give the captioned compound (21.0 g, 82%). Mp. 170-171° C. $^1$H-NMR (DMSO-$d_6$) δ: 1.34 (t, J=7.0 Hz, 3H), 4.34 (q, J=7.0 Hz, 2H), 6.43 (d, J=15.5 Hz, 1H), 7.53-7.56 (m, 1H), 7.62-7.65 (m, 1H), 7.84-7.89 (m, 2H), 8.24 (d, J=15.5 Hz, 1H), 12.52 (s, 1H).

Example 60

Production of (E)-3-(2-Ethoxycarbonylphenyl)-N-[2-(imidazol-1-yl)ethyl]-2-propenamide The same procedures as those in Compound 22 were carried out from the compound obtained in Example 59 (8.0 g, 37 mmol), 1-(2-aminoethyl)imidazole (4.5 g, 40 mmol), WSC.HCl (8.4 g, 44 mmol), and methylene chloride (400 mL), to give the captioned compound (7.3 g, 64%) as crystals. Mp. 135-136° C. $^1$H-NMR (DMSO-$d_6$) δ: 1.33 (t, J=7.0 Hz, 3H), 3.52 (q, J=7.0 Hz, 2H), 4.11 (t, J=6.0 Hz, 2H), 4.30-4.35 (m, 2H), 6.52 (d, J=15.5 Hz, 1H), 6.90 (s, 1H), 7.18 (s, 1H), 7.49-7.52 (m, 1H), 7.61-7.68 (m, 3H), 7.84 (d, J=7.5 Hz, 1H), 8.05 (d, J=15.5 Hz, 1H), 8.31 (t, J=5.5 Hz, 1H).

Example 61

Production of (E)-3-(2-Carboxyphenyl)-N-[(2-imidazol-1-yl)ethyl]-2-propenamide (Compound 47)

A 1 mol/L aqueous sodium hydroxide solution (4.8 mmol, equivalent to NaOH 4.8 mmol) was added dropwise to an ethanol (50 mL) solution of the compound obtained in Example 60 (1.0 g, 3.2 mmol) at room temperature, and the mixture was stirred at 50° C. for 3 hours. Water was added to the residue obtained by distilling off the solvent under a reduced pressure, and the solution was neutralized with DIAION SK-116H$^+$ Foam. The ion-exchange resin was filtered away with a Millipore filter, and the filtrate was then distilled off under a reduced pressure, to give the captioned compound (0.6 g, 71%) as an amorphous solid.

Example 62

Production of 2-[2-(2-Butylimidazol-1-yl)ethyl]isoindole-1,3-dione

The same procedures as in Example 47 were carried out from 2-butylimidazole (5.0 g, 40 mmol), N-(2-bromoethyl)phthalimide (15.4 g, 60 mmol), anhydrous potassium carbonate (8.4 g, 64 mmol) and DMF (100 mL), to give the captioned compound (4.6 g, 39%) as an amorphous solid. $^1$H-NMR (DMSO-$d_6$) δ: 0.80 (t, J=7.3 Hz, 3H), 1.22-1.26 (m, 2H), 1.52-1.55 (m, 2H), 2.49-2.53 (m, 2H), 3.87 (t, J=6.2 Hz, 2H), 4.16 (t, J=6.2 Hz, 2H), 6.67 (s, 1H), 6.97 (s, 1H), 7.83-7.87 (m, 4H).

Example 63

Production of 2-(2-Butylimidazol-1-yl)ethylamine

The same procedures as in Example 48 were carried out from the compound obtained in Example 62 (4.0 g, 14 mmol), hydrazine monohydrate (1.3 mL, 27 mmol), and ethanol (80 mL), to give the captioned compound (2.0 g, 89%) as an oily product. $^1$H-NMR (DMSO-d$_6$) δ: 0.89 (t, J=7.3 Hz, 3H), 1.32-1.36 (m, 2H), 1.60-1.63 (m, 2H), 2.58-2.61 (m, 2H), 2.78 (t, J=6.7 Hz, 2H), 3.81 (t, J=6.7 Hz, 2H), 6.72 (s, 1H), 7.01 (s, 1H).

Example 64

Production of (E)-N-[2-(2-Butylimidazol-1-yl)ethyl]-3-(2-fluorophenyl)-2-propenamide The same procedures as those in Compound 22 were carried out from 2-fluorocinnamic acid (1.8 g, 11 mmol), the compound obtained in Example 63 (2.0 g, 12 mmol), WSC.HCl (2.5 g, 13 mmol), and methylene chloride (130 mL), to give the captioned compound (2.0 g, 59%) as an oily product. $^1$H-NMR (DMSO-d$_6$) δ: 0.85 (t, J=7.3 Hz, 3H), 1.29-1.34 (m, 2H), 1.59-1.62 (m, 2H), 2.57 (t, J=7.5 Hz, 2H), 3.43-3.46 (m, 2H), 4.00 (t, J=6.2 Hz, 2H), 6.70 (d, J=16.0 Hz, 1H), 6.75 (s, 1H), 7.04 (s, 1H), 7.26-7.30 (m, 2H), 7.40-7.50 (m, 1H), 7.51 (d, J=16.0 Hz, 1H), 7.60-7.70 (m, 1H), 8.39 (s, 1H).

Example 65

Production of (E)-3-(2-Fluorophenyl)-N-[2-(2-butylimidazol-1-yl)ethyl]-2-propenamide hydrochloride (Compound 48)

The same procedures as those in Compound 43 were carried out from the compound obtained in Example 64 (2.0 g, 6.3 mmol), a 4 mol/L hydrogen chloride-dioxane solution (4.8 mL, equivalent to HCl 19 mmol), and methylene chloride (30 mL), to give the captioned compound (2.2 g, 99%) as an amorphous solid.

Example 66

Production of (E)-3-(3-Methoxycarbonylphenyl)-2-propenoic acid

The same procedures as in Example 59 were carried out from methyl 3-formylbenzoate (5.0 g, 30 mmol), malonic acid (4.7 g, 45 mmol), piperidine (0.3 g, 3.0 mmol) and pyridine (100 mL), to give the captioned compound (4.7 g, 76%) as crystals. Mp. 195-197° C. $^1$H-NMR (DMSO-d$_6$) δ: 3.88 (s, 3H), 6.62 (d, J=16.0 Hz, 1H), 7.55-7.70 (m, 2H), 7.95-8.03 (m, 2H), 8.19 (s, 1H).

Example 67

Production of (E)-3-(3-Methoxycarbonylphenyl)-N-[2-(imidazol-1-yl)ethyl]-2-propenamide The same procedures as those in Compound 22 were carried out from the compound obtained in Example 66 (1.5 g, 7.0 mmol), 1-(2-aminoethyl)imidazole (0.8 g, 6.0 mmol), WSC.HCl (1.5 g, 8.0 mmol), and methylene chloride (50 mL), to give the captioned compound (1.2 g, 33%) as an amorphous solid. $^1$H-NMR (DMSO-d$_6$) δ: 3.52 (t, J=6.0 Hz, 2H), 3.88 (s, 3H), 4.10 (t, J=6.0 Hz, 2H), 6.73 (d, J=16.0 Hz, 1H), 6.89 (s, 1H), 7.18 (s, 1H), 7.46-7.62 (m, 3H), 7.83 (t, J=7.7 Hz, 1H), 7.94 (t, J=7.7 Hz, 1H), 8.14 (s, 1H), 8.29 (t, J=5.8 Hz, 1H).

Example 68

Production of (E)-3-(3-Carboxyphenyl)-N-[(2-imidazol-1-yl)ethyl]-2-propenamide hydrochloride (Compound 49)

An aqueous solution (50 ml) of sodium hydroxide (0.3 g, 7.0 mmol) was added to a methanol (30 mL) solution of the compound obtained in Example 67 (0.6 g, 2.0 mmol) at room temperature, and the mixture was stirred at 80° C. for 3 hours. The reaction mixture was made acidic with a diluted hydrochloric acid, and the solvents were then distilled off under a reduced pressure. The residue was dissolved in methanol, insoluble substances were filtered away, and the solvents were then distilled off under a reduced pressure. The obtained residue was dissolved in methylene chloride (10 mL), and a 4 mol/L hydrogen chloride-dioxane solution (3 mL, equivalent to HCl 12 mmol) was added dropwise thereto at room temperature. The mixture was stirred in that state for 24 hours, and the solvents were then distilled off under a reduced pressure, to give the captioned compound (0.8 g, 99%) as crystals.

Example 69

Production of (E)-3-(4-Methoxycarbonylphenyl)-2-propenoic acid

The same procedures as in Example 59 were carried out from methyl 4-formylbenzoate (5.0 g, 30 mmol), malonic acid (4.7 g, 45 mmol), piperidine (0.3 g, 3.0 mmol) and pyridine (100 mL), to give the captioned compound (6.0 g, 97%) as crystals. Mp. 246-248° C. $^1$H-NMR (DMSO-d$_6$) δ: 3.87 (s, 3H), 6.66 (d, J=16.0 Hz, 1H), 7.64 (d, J=16.0 Hz, 1H), 7.82-7.84 (m, 2H), 7.96-7.98 (m, 2H).

Example 70

Production of (E)-3-(4-Methoxycarbonylphenyl)-N-[2-(imidazol-1-yl)ethyl]-2-propenamide The same procedures as those in Compound 22 were carried out from the compound obtained in Example 69 (1.2 g, 6.0 mmol), 1-(2-aminoethyl)imidazole (0.6 g, 5.0 mmol), WSC.HCl (1.5 g, 8.0 mmol), and methylene chloride (50 mL), to give the captioned compound (1.2 g, 80%) as an amorphous solid. $^1$H-NMR (DMSO-d$_6$) δ: 3.51-3.53 (m, 2H), 3.86 (s, 3H), 4.09-4.11 (m, 2H), 6.73 (d, J=16.0 Hz, 1H), 6.89 (s, 1H), 7.17 (s, 1H), 7.48 (d, J=16.0 Hz, 1H), 7.60 (s, 1H), 7.70 (d, J=7.7 Hz, 2H), 7.98 (d, J=7.7 Hz, 2H).

Example 71

Production of (E)-3-(4-Carboxyphenyl)-N-[(2-imidazol-1-yl)ethyl]-2-propenamide hydrochloride (Compound 50)

The same procedures as those in Compound 49 were carried out from the compound obtained in Example 70 (1.0 g, 3.0 mmol), sodium hydroxide (0.2 g, 5.0 mmol), methanol (30 mL), water (5.0 mL), methylene chloride (10 mL), and a 4 mol/L hydrogen chloride-dioxane solution (3.0 mL), to give the captioned compound (1.2 g, 99%) as crystals.

Example 72

Production of (E)-3-(2-Fluorophenyl)-2-propenoyl chloride

Oxalyl chloride (3.8 g, 30 mmol) was added to a methylene chloride (50 mL) solution of 2-fluorocinnamic acid (1.0 g, 6.0 mmol) at 0° C., and the mixture was stirred at room temperature for 18 hours. The solvent was distilled off under a reduced pressure, to give the captioned compound (1.0 g, 91%) as an oily product. This compound was used in the subsequent reaction without purification.

Example 73

Production of (E)-3-(2-Fluorophenyl)-N-[4-(2H-pyrazol-3-yl)phenyl]-2-propenamide (Compound 51)

An anhydrous THF (25 mL) solution of the compound obtained in Example 72 (0.5 g, 3.0 mmol) was added dropwise to an anhydrous THF (25 mL) solution of 5-[4-(aminophenyl)]-2H-pyrazole (0.7 g, 4.0 mmol) at 0° C., and the mixture was stirred at room temperature for 1 hour. Methanol (50 mL) was added to the reaction mixture, and the sedimentations were removed by decantation. The residue obtained by distilling off the solvent under a reduced pressure was purified with silica gel column chromatography (NH, n-hexane:ethyl acetate=1:1). The intended product was crystallized from petroleum ether, to give the captioned compound (0.2 g, 25%).

Compounds. 52 to 56 were produced in the same manner as this compound from appropriate starting compounds.

Example 74

Production of (E)-N-3-Morpholinopropyl)-3-(2-trifluoromethylphenyl)-2-propenamide The same procedures as those in Compound 22 were carried out from 2-trifluoromethylcinnamic acid (2.5 g, 12 mmol), 3-morpholinopropylamine (1.9 mL, 17 mmol), WSC.HCl (2.7 g, 14 mmol), and methylene chloride (100 mL), to give the captioned compound (2.8 g, 71%) as an oily product. $^1$H-NMR (DMSO-$d_6$) δ: 1.61-1.64 (m, 2H), 2.29-2.34 (m, 6H), 3.21-3.22 (m, 2H), 3.56-3.58 (m, 4H), 6.68 (d, J=15.5 Hz, 1H), 7.59-7.83 (m, 5H), 8.26 (s, 1H).

Example 75

Production of (E)-N-(3-Morpholinopropyl)-3-(2-trifluoromethylphenyl)-2-propenamide hydrochloride (Compound 57)

A 4 mol/L hydrogen chloride-dioxane solution (4.0 mL, equivalent to HCl 16 mmol) was added dropwise to a methylene chloride (40 mL) solution of the compound obtained in Example 74 (2.8 g, 8.2 mmol) at room temperature, and the mixture was stirred in that state for 1 hour. Diethyl ether was added to the residue obtained by distilling off the solvent under a reduced pressure, and the precipitated crystals were collected by filtration, to give the captioned compound (2.6 g, 84%).

Example 76

Production of (E)-2-Cyano-3-(4-fluorophenyl)-2-propenoic acid

Cyanoacetic acid (7.2 g, 85 mmol) and piperidine (9.0 mL, 85 mmol) were added to an ethanol (200 mL) solution of 4-fluorobenzoic acid (10.0 g, 81 mmol) at room temperature, and the mixture was stirred at 60° C. for 3 hours. Water was added to the residue obtained by distilling off the solvent under a reduced pressure, and the solution was made acidic with a diluted hydrochloric acid. The precipitated crystals were collected by filtration, and washed with water, to give the captioned compound (13.2 g, 88%). Mp. 192-193° C. $^1$H-NMR (DMSO-$d_6$) δ: 7.44-7.48 (m, 2H), 8.13-8.16 (m, 2H), 8.37 (s, 1H), 13.85-14.20 (br, 1H).

Example 77

Production of 2,5-Dioxopyrrolidin-1-yl (E)-2-cyano-3-(4-fluorophenyl)-2-propenoate The same procedures as those in Compound 22 were carried out from the compound obtained in Example 76 (5.0 g, 26 mmol), HOSu (4.5 g, 39 mmol), WSC.HCl (7.5 g, 39 mmol), and methylene chloride (150 mL), to give the captioned compound (3.1 g, 42%) as crystals. Mp. 159-160° C. $^1$H-NMR (DMSO-$d_6$) δ: 2.91 (s, 4H), 7.51-7.55 (m, 2H), 8.57-8.29 (m, 2H), 8.75 (s, 1H).

Example 78

Production of (E)-2-Cyano-3-(4-fluorophenyl)-N-(3-morpholinopropyl)-2-propenamide (Compound 58)

A THF (5.0 mL) solution of 3-morpholinopropylamine (1.0 mL, 6.9 mmol) was added dropwise to a THF (20 mL) solution of the compound obtained in Example 77 (1.0 g, 3.5 mmol) at room temperature, and the mixture was stirred in that state for 1 hour. The precipitated crystals were filtered away. Thereafter, the residue obtained by distilling off the solvent of the filtrate under a reduced pressure was purified with silica gel column chromatography (PSQ100B, chloroform:methanol=60:1), to give the captioned compound (0.3 g, 26%) as crystals.

Example 79

Production of 2-[3-(Piperidin-1-yl)propyl]isoindole-1,3-dione

A toluene (300 mL) solution of N-(3-bromopropyl) phthalimide (10.0 g, 37 mmol) and piperidine (8.1 mL, 82 mmol) was heated under refluxing for 2 hours. The residue obtained by distilling off the solvent under a reduced pressure was dissolved in ethyl acetate, the solution was washed with water, and an organic layer was then dried over anhydrous sodium sulfate. The residue obtained by distilling of the solvents under a reduced pressure was purified with silica gel column chromatography (PSQ100B, chloroform:methanol=50:1), to give the captioned compound (6.7 g, 67%) as an oily product. $^1$H-NMR (DMSO-$d_6$) δ: 1.20-1.30 (m, 6H), 1.71-1.74 (m, 2H), 2.18-2.27 (m, 6H), 3.63 (t, J=6.8 Hz, 2H), 7.82-7.88 (m, 4H).

Example 80

Production of [3-(Piperidin-1-yl)]propylamine

The same procedures as in Example 48 were carried out from the compound obtained in Example 79 (6.7 g, 25 mmol), hydrazine monohydrate (2.4 mL, 50 mmol), and ethanol (250 mL), to give the captioned compound (1.9 g, 55%) as an oily product. $^1$H-NMR (DMSO-$d_6$) δ: 1.43-1.52 (m, 2H), 1.63-1.70 (m, 6H), 2.34-2.43 (m, 6H), 2.63 (t, J=7.1 Hz, 2H).

Example 81

Production of (E)-3-(2-Fluorophenyl)-N-[3-(1-piperidyl)propyl]-2-propenamide hydrochloride (Compound 59)

The same procedures as those in Compound 22 were carried out from the compound obtained in Example 80 (1.9 g, 14 mmol), 2-fluorocinnamic acid (2.2 g, 13 mmol), WSC.HCl (3.0 g, 16 mmol), and methylene chloride (100 mL), to give an oily product. The oily product (3.0 g, 10 mmol) was dissolved in methylene chloride (80 mL), and a 4 mol/L hydrogen chloride-dioxane solution (5.2 mL, equivalent to HCl 21 mmol) was added dropwise thereto at room temperature, and the mixture was stirred at room temperature for 30 minutes. The precipitated crystals were collected by filtration, and washed with diethyl ether, to give the captioned compound (2.9 g, 68%).

Example 82

Production of 2-[3-(Thiomorpholin-4-yl)propyl]isoindole-1,3-dione

The same procedures as in Example 79 were carried out from N-(3-bromopropyl)phthalimide (10.0 g, 37 mmol), thiomorpholine (7.8 mL, 82 mmol), and toluene (300 mL), to give the captioned compound (7.1 g, 66%) as an oily product. $^1$H-NMR (DMSO-$d_6$) δ: 1.72-1.74 (m, 2H), 2.31-2.39 (m, 6H), 2.49-2.51 (m, 4H), 3.63 (t, J=6.8 Hz, 2H), 7.83-7.88 (m, 4H).

Example 83

Production of 3-(Thiomorpholin-4-yl)propylamine

The same procedures as in Example 48 were carried out from the compound obtained in Example 82 (7.1 g, 25 mmol), hydrazine monohydrate (2.4 mL, 49 mmol) and ethanol (250 mL), to give the captioned compound (2.5 g, 65%) as an oily product. $^1$H-NMR (MeOD) δ: 1.63-1.68 (m, 2H), 2.41-2.63 (m, 2H), 2.63-2.73 (m, 10H).

Example 84

Production of (E)-3-(4-Fluorophenyl)-N-(3-thiomorpholinopropyl)-2-propenamide (Compound 60)

The same procedures as those in Compound 22 were carried out from the compound obtained in Example 83 (2.4 g, 15 mmol), 4-fluorocinnamic acid (2.3 g, 14 mmol), WSC.HCl (3.2 g, 19 mmol), and methylene chloride (100 mL), to give the captioned compound (2.9 g, 67%) as crystals.

Example 85

Production of (E)-3-(2-Fluorophenyl)-N-3-thiomorpholinopropyl)-2-propenamide

The same procedures as those in Compound 22 were carried out from the compound obtained in Example 83 (2.5 g, 16 mmol), 2-fluorocinnamic acid (2.4 g, 14 mmol), WSC.HCl (3.3 g, 17 mmol), and methylene chloride (100 mL), to give the captioned compound (3.7 g, 84%) as an oily product. $^1$H-NMR (DMSO-$d_6$) δ: 1.59-1.62 (m, 2H), 2.32-2.35 (m, 2H), 2.59-2.62 (m, 8H), 3.17-3.21 (m, 2H), 6.72 (d, J=16.0 Hz, 1H), 7.25-7.30 (m, 2H), 7.42-7.50 (m, 2H), 7.64-7.67 (m, 1H), 8.22 (t, J=5.5 Hz, 1H).

Example 86

Production of (E)-3-(2-Fluorophenyl)-N-(3-thiomorpholinopropyl)-2-propenamide hydrochloride (Compound 61)

The same procedures as those in Compound 59 were carried out from the compound obtained in Example 85 (3.7 g, 12 mmol), a 4 mol/L hydrogen chloride-dioxane solution (6.0 mL, equivalent to HCl 24 mmol), and methylene chloride (100 mL), to give the captioned compound (3.7 g, 89%) as crystals.

Example 87

Production of 2-[3-(1,1-Dioxothiomorpholin-4-yl)propyl]isoindole-1,3-dione

The same procedures as in Example 79 were carried out from N-(3-bromopropyl)phthalimide (10.0 g, 37 mmol), 1,1-dioxothiomorpholine (11.1 g, 82 mmol), DIPEA (9.7 mL, 56 mmol), and toluene (300 mL), to give the captioned compound (9.9 g, 82%) as crystals. Mp. 172-173° C. $^1$H-NMR (DMSO-$d_6$) δ: 1.73-1.76 (m, 2H), 2.48-2.51 (m, 2H), 2.80-2.82 (m, 4H), 2.93-2.95 (m, 4H), 3.63-3.66 (m, 2H), 7.83-7.89 (m, 4H).

Example 88

Production of 3-(1,1-Dioxothiomorpholin-4-yl)propylamine

The same procedures as in Example 48 were carried out from the compound obtained in Example 87 (9.0 g, 28 mmol), hydrazine monohydrate (2.7 mL, 56 mmol), and ethanol (300 mL), to give the captioned compound (4.6 g, 86%) as an oily product. $^1$H-NMR (DMSO-$d_6$) δ: 1.46-1.49 (m, 2H), 2.45-2.49 (m, 2H), 2.52-2.55 (m, 2H), 2.83-2.86 (m, 4H), 3.05-3.07 (m, 4H).

Example 89

Production of (E)-N-[3-(1,1-Dioxo-1,4-thiazinan-4-yl)propyl]-3-(2-fluorophenyl)-2-propenamide The same procedures as those in Compound 22 were carried out from the compound obtained in Example 88 (2.5 g, 13 mmol), 2-fluorocinnamic acid (2.0 g, 12 mmol), WSC.HCl (2.7 g, 14 mmol), and methylene chloride (80 mL), to give the captioned compound (2.6 g, 64%) an oily product. $^1$H-NMR (DMSO-$d_6$) δ: 1.60-1.63 (m, 2H), 2.48-2.51 (m, 2H), 2.87-2.89 (m, 4H), 3.07-3.09 (m, 4H), 3.19-

3.23 (m, 2H), 6.72 (d, J=16.0 Hz, 1H), 7.25-7.30 (m, 2H), 7.42-7.50 (m, 2H), 7.64-7.67 (m, 1H), 8.22 (t, J=5.4 Hz, 1H).

Example 90

Production of (E)-N-[3-(1,1-Dioxo-1,4-thiazinan-4-yl)propyl]-3-(2-fluorophenyl)-2-propenamide hydrochloride (Compound 62)

The same procedures as those in Compound 61 were carried out from the compound obtained in Example 89 (2.6 g, 7.7 mmol), a 4 mol/L hydrogen chloride-dioxane solution (4.0 mL, equivalent to HCl 16 mmol), and methylene chloride (60 mL), to give the captioned compound (2.3 g, 79%) as crystals.

Example 91

Production of (E)-N-[3-(1,1-Dioxo-1,4-thiazinan-4-yl)propyl]-3-(4-fluorophenyl)-2-propenamide The same procedures as those in Compound 22 were carried out from the compound obtained in Example 88 (2.0 g, 10 mmol), 4-fluorocinnamic acid (1.5 g, 9.2 mmol), WSC.HCl (2.1 g, 11 mmol), and methylene chloride (60 mL), to give the captioned compound (1.8 g, 59%) as an oily product. $^1$H-NMR (DMSO-$d_6$) δ: 1.59-1.61 (m, 2H), 2.47-2.50 (m, 2H), 2.86-2.88 (m, 4H), 3.07-3.09 (m, 4H), 3.18-3.22 (m, 2H), 6.56 (d, J=15.8 Hz, 1H), 7.23-7.27 (m, 2H), 7.41 (d, J=15.8 Hz, 1H), 7.61-7.63 (m, 2H), 8.09 (t, J=5.5 Hz, 1H).

Example 92

Production of (E)-N-[3-(1,1-Dioxo-1,4-thiazinan-4-yl)propyl]-3-(4-fluorophenyl)-2-propenamide hydrochloride (Compound 63)

The same procedures as those in Compound 58 were carried out from the compound obtained in Example 91 (1.8 g, 5.4 mmol), a 4 mol/L hydrogen chloride-dioxane solution (2.7 mL, equivalent to HCl 11 mmol), and methylene chloride (50 mL), to give the captioned compound (1.6 g, 79%) as crystals.

Example 93

Production of (E)-N-[3-(Cyclohexylamino)propyl]-3-(2-fluorophenyl)-2-propenamide A THF (30 mL) solution of N-cyclohexyl-1,3-propanediamine (3.9 mL, 23 mmol) was added dropwise to a THF (100 mL) solution of (2,5-dioxopyrrolidin-1-yl) (E)-3-(2-fluorophenyl)-2-propenoate (3.0 g, 11 mmol) at 0° C., and the mixture was stirred at room temperature for 1 hour. The precipitated crystals were filtered away, and the solvent of the filtrate was then distilled off under a reduced pressure. The obtained residue was dissolved in ethyl acetate, the solution was washed with water, and an organic layer was then dried over anhydrous sodium sulfate. The residue obtained by distilling off the solvents under a reduced pressure was purified with silica gel column chromatography (NH, chloroform), to give the captioned compound (2.9 g, 84%) as an oily product. $^1$H-NMR (DMSO-$d_6$) δ: 0.96-1.21 (m, 5H), 1.34-1.36 (m, 1H), 1.53-1.59 (m, 3H), 1.64-1.67 (m, 2H), 1.78-1.81 (m, 2H), 2.29-2.32 (m, 1H), 2.51-2.55 (m, 2H), 3.20-3.24 (m, 2H), 6.72 (d, J=16.0 Hz, 1H), 7.25-7.30 (m, 2H), 7.42-7.49 (m, 2H), 7.63-7.67 (m, 1H), 8.24 (t, J=5.5 Hz, 1H).

Example 94

Production of (E)-N-[(3-Cyclohexylamino)propyl]-3-(2-fluorophenyl)-2-propenamide hydrochloride (Compound 64)

The same procedures as those in Compound 59 were carried out from the compound obtained in Example 93 (2.9 g, 9.6 mmol), a 4 mol/L hydrogen chloride-dioxane solution (4.8 mL, equivalent to HCl 19 mmol), and methylene chloride (80 mL), to give the captioned compound (2.9 g, 91%) as crystals.

Example 95

Production of (E)-3-(2-Fluorophenyl)-N-(4-guanidinobutyl)-2-propenamide hydrochloride (Compound 65)

An aqueous solution (30 mL) of sodium hydroxide (0.4 g, 10 mmol) was added to a methylene chloride (30 mL) solution of Compound 14 (1.8 g, 8.0 mmol) at room temperature, and the mixture was stirred in that state for 1 hour. The reaction mixture was extracted with methylene chloride, and an organic layer was dried over anhydrous sodium sulfate. The residue obtained by distilling off the solvents under a reduced pressure was dissolved in DMF (10 mL), N-(1H-pyrazol-1-yl)guanidine (1.2 g, 8.0 mmol) and triethylamine (3.6 g, 36 mmol) were then added to the solution at room temperature, and the mixture was stirred for 72 hours. Diethyl ether (100 mL) was added to the reaction mixture, and an upper layer was removed by decantation. Thereafter, the solvents were distilled off under a reduced pressure, to give an oily product. A 4 mol/L hydrogen chloride-dioxane solution (13 mL, equivalent to HCl 52 mmol) was added to the obtained residue at room temperature, and the mixture was stirred in that state for 3 hours. Methanol and methylene chloride were added to the residue obtained by distilling off the solvents under a reduced pressure, and the precipitated crystals were collected by filtration, to give the captioned compound (1.8 g, 75%).

Example 96

Production of Methyl 3-{[(E)-3-(2-fluorophenyl)-2-propenoyl]amino}-propanoate

The same procedures as those in Compound 22 were carried out from 2-fluorocinnamic acid (8.3 g, 50 mmol), methyl 3-aminopropionate hydrochloride (7.0 g, 50 mmol), WSC.HCl (10.5 g, 55 mmol), triethylamine (6.0 g, 60 mmol), and methylene chloride (300 mL), to give the captioned compound (9.7 g, 78%) as an oily product. $^1$H-NMR (DMSO-$d_6$) δ: 2.55 (t, J=6.5 Hz, 2H), 3.41 (t, J=6.5 Hz, 2H), 3.62 (s, 3H), 6.72 (d, J=16.0 Hz, 1H), 7.24-7.30 (m, 2H), 7.42-7.51 (m, 2H), 7.63-7.67 (m, 1H).

Example 97

Production of 3-{[(E)-3-(2-Fluorophenyl)-2-propenoyl]amino}propanoic acid (Compound 66)

A 1 mol/L aqueous sodium hydroxide solution was added dropwise to an ethanol (160 mL) solution of the compound obtained in Example 96 (1.0 g, 4.0 mmol) at room temperature. The mixture was heated under refluxing for 2 hours, and insoluble substances were filtered away under heating. The solvent of the filtrate was distilled off under a reduced pressure, water was then added to the residue, and the solution was made acidic with a diluted hydrochloric acid. The precipitated crystals were collected by filtration, and dissolved in diethyl ether, and the solution was back-extracted with a 1 mol/L aqueous sodium hydroxide solution. An aqueous layer was made acidic with a diluted hydrochloric acid, and the precipitated crystals were collected by filtration and washed with water, to give the captioned compound (950 mg, 99%).

Example 98

Production of 2-(3-Thiomorpholinopropyl)isoindoline-1,3-dione

N,N-Diisopropylethylamine (39 mL) was added to a toluene (800 mL) solution of N-(3-bromopropyl)phthalimide (39.0 g, 0.15 mol) and thiomorpholine (30 mL) at room temperature, and the mixture was heated under refluxing for 8 hours. Ethyl acetate (500 mL) was added to the residue obtained by distilling off the solvent under a reduced pressure, and the mixture was washed with water. An organic layer was dried over anhydrous sodium sulfate. Thereafter, the residue obtained by distilling off the solvents under a reduced pressure was purified with silica gel column chromatography (chloroform), to give the captioned compound (37.3 g, 88%) as an oily product. $^1$H-NMR (DMSO-$d_6$) δ: 1.70-1.78 (m, 2H), 2.32-2.39 (m, 6H), 2.49-2.51 (m, 4H), 3.61 (t, J=6.8 Hz, 2H), 7.83-7.88 (m, 4H).

Example 99

Production of 2-[3-(1-Oxo-1,4-thiazinan-4-yl)propyl]isoindoline-1,3-dione

A methylene chloride (140 mL) solution of mCPBA (9.8 g, 57 mmol) was added dropwise to a methylene chloride (220 mL) solution of the compound obtained in Example 98 (15.0 g, 52 mmol), under ice-cooling over 30 minutes, and the mixture was then stirred at room temperature for 20 hours. The reaction mixture was sequentially washed with a saturated aqueous sodium hydrogensulfite solution, a saturated sodium hydrogencarbonate solution, and a saturated sodium chloride solution, and an organic layer was then dried over anhydrous sodium sulfate. The residue obtained by distilling off the solvents under a reduced pressure was purified with silica gel column chromatography (chloroform:methanol=50:1), to give the captioned compound (5.9 g, 37%) as a solid. Mp 95-96° C. $^1$H-NMR (DMSO-$d_6$) δ: 1.70-1.80 (m, 2H), 2.38-2.48 (m, 2H), 2.50-2.64 (m, 6H), 2.77-3.33 (m, 2H), 3.64 (t, J=6.8 Hz, 2H), 7.83-7.88 (m, 4H).

Example 100

Production of 3-(Oxo-1,4-thiazinan-4-yl)propan-1-amine

Hydrazine monohydrate (1.9 mL, 38 mmol) was added to an ethanol (180 mL) solution of the compound obtained in Example 99 (5.8 g, 19 mmol) at room temperature, and the mixture was heated under refluxing for 5 hours. The reaction mixture was cooled to room temperature, and the precipitated solid was filtered away. Thereafter, methylene chloride (50 mL) was added to the residue obtained by distilling off the solvent of the filtrate under a reduced pressure, and insoluble substances were filtered away. Methylene chloride (30 mL) was added to the residue obtained by distilling off the solvents of the filtrate under a reduced pressure, and insoluble substances were again filtered away. The solvents of the filtrate were distilled off under a reduced pressure, to give the captioned compound (3.3 g, 98%) as an oily product. $^1$H-NMR (DMSO-$d_6$) δ: 1.53-1.55 (m, 2H), 2.37-2.50 (m, 2H), 2.57-2.61 (m, 4H), 2.68-2.72 (m, 2H), 2.78-2.85 (m, 4H).

Example 101

Production of (E)-3-(2-Fluorophenyl)-N-[3-(1-oxo-1,4-thiazinan-4-yl)propyl]-2-propenamide WSC.HCl (3.9 g, 20 mmol) was added to a methylene chloride (100 mL) suspension of 2-fluorocinnamic acid (2.8 g, 17 mmol) and the compound obtained in Example 100 (3.3 g, 19 mmol), under ice-cooling, and the mixture was stirred at room temperature for 16 hours. The reaction mixture was washed with water and a saturated sodium chloride solution, and an organic layer was then dried over anhydrous sodium sulfate. The residue obtained by distilling off the solvents under a reduced pressure was purified with silica gel column chromatography (chloroform), to give the captioned compound (3.5 g, 63%) as an oily product. $^1$H-NMR (DMSO-$d_6$) δ: 1.62-1.64 (m, 2H), 2.38-2.41 (m, 2H), 2.41-2.64 (m, 4H), 2.71-2.87 (m, 4H), 3.19-3.22 (m, 2H), 6.72 (d, J=16.0 Hz, 1H), 7.25-7.03 (m, 2H), 7.42-7.47 (m, 2H), 7.64-7.67 (m, 1H), 8.22 (t, J=5.5 Hz, 1H).

Example 102

Production of (E)-3-(4-Fluorophenyl)-N-[3-(1-oxo-1,4-thiazinan-4-yl)propyl]-2-propenamide (Compound 67)

The same procedures as in Example 101 were carried out from 4-fluorocinnamic acid (1.1 g, 6.5 mmol), the compound obtained in Example 100 (1.3 g, 7.2 mmol), WSC.HCl (1.5 g, 7.8 mmol), and methylene chloride (40 mL), to give the captioned compound (0.8 g, 38%) as a solid.

Example 103

Production of (E)-3-(2-Fluorophenyl)-N-[3-(1-oxo-1,4-thiazinan-4-yl)propyl]-2-propenamide hydrochloride (Compound 68)

A 4 mol/L hydrogen chloride-dioxane solution (5.3 mL, equivalent to HCl 21 mmol) was added dropwise to a methylene chloride (80 mL) solution of the compound obtained in Example 101 (3.4 g, 11 mmol) at room temperature over 3 minutes, and the mixture was stirred in that state for 1 hour. The precipitated solid was collected by filtration, and washed with diethyl ether, to give the captioned compound (3.6 g, 96%).

Example 104

Production of tert-Butyl N-[(3-bromophenyl)methyl]carbamate

A methylene chloride (40 mL) solution of Boc$_2$O (21.2 g, 97 mmol) was added dropwise to a methylene chloride (160 mL) solution of 3-bromobenzylamine (15.0 g, 81 mmol) and triethylamine (23 mL, 162 mmol) over 20 minutes, under ice-cooling, and the mixture was stirred at room temperature for 5 hours. The reaction mixture was washed with water, and an organic layer was then dried over anhydrous sodium sulfate. n-Hexane was added to the residue obtained by distilling off the solvent under a reduced pressure, and the precipitated solid was collected by filtration, to give the captioned compound (19.8 g, 92%). Mp 41-42° C. $^1$H-NMR (DMSO-$d_6$) δ: 1.39 (s, 9H), 4.12 (d, J=6.1 Hz, 2H), 7.23-7.28 (m, 2H), 7.40-7.42 (m, 3H).

Example 105

Production of tert-Butyl N-[(3-thiomorpholinophenyl)methyl]carbamate

Thiomorpholine (9.9 mL, 105 mmol), palladium acetate (0.8 g, 3.5 mmol), 2-(di-tert-butylphosphino)biphenyl (2.1 g, 7.0 mmol), and sodium tert-butoxide (3.7 g, 38 mmol) were added to a toluene (70 mL) solution of the compound obtained in Example 104 (10.0 g, 35 mmol), in an argon atmosphere at room temperature, and the mixture was stirred at 80° C. for 5 hours. The reaction mixture was cooled to room temperature, and the precipitated solid was filtered away. The residue obtained by distilling off the solvent of the filtrate under a reduced pressure was purified with silica gel column chromatography (n-hexane:ethyl acetate=5:1), to give the captioned compound (3.1 g, 28%) as a solid. Mp 62-63° C. $^1$H-NMR (DMSO-$d_6$) δ: 1.39 (s, 9H), 2.64-2.66 (m, 4H), 3.48-3.50 (m, 4H), 4.06 (d, J=6.1 Hz, 2H), 6.64 (d, J=7.4 Hz, 1H), 6.77-6.79 (m, 2H), 7.12-7.16 (m, 1H), 7.30 (t, J=5.9 Hz, 1H).

Example 106

Production of (3-Thiomorpholinophenyl)methanamine dihydrochloride

A 4 mol/L hydrogen chloride-dioxane solution (12 mL, equivalent to HCl 48 mmol) was added dropwise to a methylene chloride (60 mL) solution of the compound obtained in Example 105 (1.5 g, 4.9 mmol) over 5 minutes at room temperature, and the mixture was mixed in that state for 1 hour. Diethyl ether was added to the residue obtained by distilling off the solvent under a reduced pressure, and the precipitated solid was collected by filtration, to give the captioned compound (1.3 g, 98%). Mp 242-243° C. MS (EI): m/z 208 [M]$^+$ (free form). $^1$H-NMR (DMSO-$d_6$) δ: 2.90-3.10 (m, 4H), 3.67-3.69 (m, 4H), 3.99 (t, J=5.6 Hz, 2H), 7.26-7.28 (m, 1H), 7.41-7.47 (m, 2H), 7.67-7.69 (m, 1H), 8.67 (s, 4H).

Example 107

Production of (E)-3-(2-Fluorophenyl)-N-[(3-thiomorpholinophenyl)methyl]-2-propenamide (Compound 69)

The same procedures as in Example 101 were carried out from the compound obtained in Example 106 (1.3 g, 4.6 mmol), 2-fluorocinnamic acid (0.77 g, 4.6 mmol), WSC.HCl (1.0 g, 5.1 mmol), and methylene chloride (40 mL), to give the captioned compound (1.0 g, 61%) as a solid.

Example 108

Production of tert-Butyl N-{[3-(1-oxo-1,4-thiazinan-4-yl)phenyl]methyl}carbamate The same procedures as in Example 99 were carried out from the compound obtained in Example 105 (1.2 g, 3.7 mmol), mCPBA (1.0 g, 4.1 mmol), and methylene chloride (20 mL), to give the captioned compound (0.9 g, 71%) as a solid. Mp 94-95° C. MS (EI): m/z 324 [M]$^+$. $^1$H-NMR (DMSO-$d_6$) δ: 1.39 (s, 9H), 2.66-2.69 (m, 2H), 2.88-2.94 (m, 2H), 3.54-3.58 (m, 2H), 3.73-3.78 (m, 2H), 4.08 (d, J=6.1 Hz, 2H), 6.67 (d, J=7.4 Hz, 1H), 6.86-6.88 (m, 2H), 7.16-7.19 (m, 1H), 7.32 (t, J=5.9 Hz, 1H).

Example 109

Production of [3-(1-Oxo-1,4-thiazinan-4-yl)phenyl]methanamine dihydrochloride

The same procedures as those in Compound 68 were carried out from the compound obtained in Example 108 (0.9 g, 2.6 mmol), a 4 mol/L hydrogen chloride-dioxane solution (6.5 mL, equivalent to HCl 26 mmol), and methylene chloride (30 mL), to give the captioned compound (0.75 g, 96%) as a solid. Mp 213-214° C. MS (EI): m/z 224 [M]$^+$ (free form). $^1$H-NMR (DMSO-$d_6$) δ: 2.73-7.76 (m, 2H), 2.97-3.02 (m, 2H), 3.64-3.67 (m, 2H), 3.83-3.88 (m, 2H), 3.94-4.00 (m, 2H), 6.97 (d, J=7.4 Hz, 1H), 7.11 (d, J=7.8 Hz, 1H), 7.28-7.34 (m, 2H), 8.56 (s, 4H).

Example 110

Production of (E)-3-(2-Fluorophenyl)-N-{[3-(oxo-1,4-thiazinan-4-yl)phenyl]methyl}-2-propenamide (Compound 70)

The same procedures as in Example 101 were carried out from the compound obtained in Example 109 (0.74 g, 2.5 mmol), 2-fluorocinnamic acid (0.41 g, 2.5 mmol), WSC.HCl (0.53 g, 2.7 mmol), and methylene chloride (20 mL), to give the captioned compound (0.38 g, 41%) as a solid.

Example 111

Production of (E)-3-(2-Fluorophenyl)-2-methyl-N-[3-(1-oxo-1,4-thiazinan-4-yl)propyl]-2-propenamide The same procedures as in Example 101 were carried out from the compound obtained in Example 100 (2.8 g, 16 mmol), (E)-3-(2-fluorophenyl)-2-methyl-2-propenoic acid (2.6 g, 14 mmol), WSC.HCl (3.3 g, 17 mmol), and methylene chloride (100 mL), to give the captioned compound (3.7 g, 75%) as an oily product. $^1$H-NMR (DMSO-$d_6$) δ: 1.64-1.67 (m, 2H), 1.93 (s, 3H), 2.39-2.41 (m, 2H), 2.62-2.65 (m, 2H), 2.71-2.74 (m, 2H), 2.82-2.86 (m, 4H), 3.18-3.22 (m, 2H), 7.18 (s, 3H), 7.23-7.27 (m, 2H), 7.39-7.44 (m, 2H), 8.08 (t, J=5.5 Hz, 1H).

Example 112

Production of (E)-3-(2-Fluorophenyl)-2-methyl-N-[3-(1-oxo-1,4-thiazinan-4-yl)propyl]-2-propenamide hydrochloride (Compound 71)

The same procedures as in Example 106 were carried out from the compound obtained in Example 111 (3.7 g, 11 mmol), a 4 mol/L hydrogen chloride-dioxane solution (8.0 mL, equivalent to HCl 32 mmol), and methylene chloride (80 mL), to give the captioned compound (3.1 g, 76%) as a solid.

The data of the properties for the compounds of the present invention produced and obtained as above are shown in Tables 1 to 8.

TABLE 1

| Compound No. | Structural Formula | Properties |
|---|---|---|
| 1 | | $^1$H-NMR (DMSO-$d_6$) δ: 2.90 (t, J = 7.4 Hz, 2H), 3.48-3.52 (m, 2H), 6.75 (d, J = 15.9 Hz, 1H), 6.99-7.00 (m, 1H), 7.06-7.09 (m, 1H), 7.18 (d, J = 1.4 Hz, 1H), 7.26-7.30 (m, 2H), 7.34-7.36 (m, 1H), 7.41-7.43 (m, 1H), 7.51-7.58 (m, 2H), 8.35 (s, 1H), 8.36 (t, J = 5.5 Hz, 1H), 10.83 (s, 1H) |
| 2 | | Mp. 115-116° C. $^1$H-NMR (DMSO-$d_6$) δ: 4.43 (d, J = 5.9 Hz, 2H), 6.78 (d, J = 16.0 Hz, 1H), 7.25-7.31 (m, 2H), 7.36-7.38 (m, 1H), 7.43-7.45 (m, 1H), 7.55 (d, J = 16.0 Hz, 1H), 7.66-7.71 (m, 2H), 8.47-8.48 (m, 1H), 8.53 (d, J = 1.6 Hz, 1H), 8.81 (t, J = 5.9 Hz, 1H) |
| 3 | | Mp. 95-96° C. $^1$H-NMR (DMSO-$d_6$) δ: 2.82 (t, J = 7.0 Hz, 2H), 3.47-3.51 (m, 2H), 6.72 (d, J = 16.0 Hz, 1H), 7.24-7.29 (m, 4H), 7.41-7.45 (m, 1H), 7.50 (d, J = 16.0 Hz, 1H), 7.63-7.66 (m, 1H), 8.34-8.36 (m, 1H), 8.48 (d, J = 4.9 Hz, 2H) |
| 4 | | Mp. 84-85° C. $^1$H-NMR (DMSO-$d_6$) δ: 1.34-1.42 (m, 2H), 1.49-1.51 (m, 4H), 2.35-2.38 (m, 6H), 3.28-3.31 (m, 2H), 6.77 (d, J = 15.9 Hz, 1H), 7.25-7.31 (m, 2H), 7.42-7.44 (m, 1H), 7.49 (d, J = 15.9 Hz, 1H), 7.65-7.68 (m, 1H), 8.12-8.14 (m, 1H) |
| 5 | | Mp. 112-113° C. $^1$H-NMR (DMSO-$d_6$) δ: 2.40-2.42 (m, 6H), 3.30-3.35 (m, 2H), 3.57-3.59 (m, 4H), 6.77 (d, J = 16.0 Hz, 1H), 7.25-7.30 (m, 2H), 7.41-7.46 (m, 1H), 7.50 (d, J = 16.0 Hz, 1H), 7.65-7.68 (m, 1H), 8.18 (t, J = 5.5 Hz, 1H) |
| 6 | | Mp. 113-114° C. $^1$H-NMR (DMSO-$d_6$) δ: 1.05-1.07 (m, 1H), 1.14-1.20 (m, 4H), 1.54-1.56 (m, 1H), 1.71-1.75 (m, 4H), 2.16-2.18 (m, 1H), 2.36-2.39 (m, 6H), 2.48-2.50 (m, 4H), 3.27-3.30 (m, 2H), 6.76 (d, J = 15.9 Hz, 1H), 7.24-7.30 (m, 2H), 7.41-7.49 (m, 2H), 7.64-7.67 (m, 1H), 8.14 (t, J = 5.5 Hz, 1H) |
| 7 | | Mp. 84-85° C. $^1$H-NMR (DMSO-$d_6$) δ: 1.04-1.19 (m, 5H), 1.54-1.61 (m, 3H), 1.70-1.74 (m, 4H), 2.14-2.16 (m, 1H), 2.26-2.29 (m, 6H), 2.47-2.51 (m, 4H), 3.18-3.21 (ra, 2H), 6.71 (d, J = 15.9 Hz, 1H), 7.24-7.29 (m, 2H), 7.41-7.49 (m, 2H), 7.63-7.66 (m, 1H), 8.24 (t, J = 5.5 Hz, 1H) |

TABLE 1-continued

| Compound No. | Structural Formula | Properties |
| --- | --- | --- |
| 8 | 2-F-C6H4-CH=CH-C(O)-NH-CH2CH2-(1-methylpyrrol-2-yl) | Mp. 93-94° C. $^1$H-NMR (DMSO-$d_6$) δ: 2.72 (t, J = 7.5 Hz, 2H), 3.37-3.41 (m, 2H), 3.52 (s, 3H), 5.81 (d, J = 3.6 Hz, 1H), 5.86-5.88 (m, 1H), 6.61-6.62 (m, 1H), 6.73 (d, J = 15.9 Hz, 1H), 7.25-7.30 (m, 2H), 7.42-7.44 (m, 1H), 7.50 (d, J = 15.9 Hz, 1H), 7.64-7.67 (m, 1H), 8.36 (t, J = 5.6 Hz, 1H) |
| 9 | 2-F-C6H4-CH=CH-C(O)-NH-CH2CH2-(pyridin-2-yl) | Mp. 86-87° C. $^1$H-NMR (DMSO-$d_6$) δ: 2.94 (t, J = 7.3 Hz, 2H), 3.54-3.58 (m, 2H), 6.71 (d, J = 16.0 Hz, 1H), 7.22-7.30 (m, 4H), 7.41-7.44 (m, 1H), 7.48 (d, J = 16.0 Hz, 1H), 7.63-7.66 (m, 1H), 7.70-7.73 (m, 1H), 8.51 (d, J = 4.7 Hz, 1H) |

TABLE 2

| Compound No. | Structural Formula | Properties |
| --- | --- | --- |
| 10 | 2-F-C6H4-CH=CH-C(O)-NH-CH2CH2-(pyridin-3-yl)·HCl | Mp. 116-117° C. $^1$H-NMR (DMSO-$d_6$) δ: 2.82 (t, J = 7.1 Hz, 2H), 3.45-3.49 (m, 2H), 6.72 (d, J = 15.9 Hz, 1H), 7.26-7.35 (m, 3H), 7.40-7.46 (m, 1H), 7.49 (d, J = 15.9 Hz, 1H), 7.65-7.68 (m, 2H), 8.35 (s, 1H), 8.43-8.47 (m, 2H) |
| 11 | 2-F-C6H4-CH=CH-C(O)-NH-(CH2)3-morpholino·HCl | Mp. 153-154° C. $^1$H-NMR (DMSO-$d_6$) δ: 1.59-1.65 (m, 2H), 2.29-2.34 (m, 6H), 3.19-3.23 (m, 2H), 3.56-3.58 (m, 4H), 6.72 (d, J = 15.9 Hz, 1H), 7.25-7.30 (m, 2H), 7.41-7.45 (m, 1H), 7.49 (d, J = 15.9 Hz, 1H), 7.64-7.67 (m, 1H), 8.24 (t, J = 5.4 Hz, 1H) |
| 12 | 2-F-C6H4-CH=CH-C(O)-NH-(CH2)3-N(Me)2·HCl | Mp. 99-100° C. $^1$H-NMR (DMSO-$d_6$) δ: 1.56-1.61 (m, 2H), 2.12 (s, 6H), 2.22 (t, J = 7.2 Hz, 2H), 3.17-3.21 (m, 2H), 6.72 (d, J = 16.0 Hz, 1H), 7.25-7.30 (m, 2H), 7.41-7.44 (m, 1H), 7.48 (d, J = 16.0 Hz, 1H), 7.64-7.67 (m, 1H), 8.23 (t, J = 5.5 Hz, 1H) |
| 13 | 2-F-C6H4-CH=CH-C(O)-NH-(CH2)4-N(Me)2·HCl | Mp. 107-108° C. $^1$H-NMR (DMSO-$d_6$) δ: 1.48-1.52 (m, 2H), 1.68-1.70 (m, 2H), 2.71 (s, 3H), 2.72 (s, 3H), 3.02-3.06 (m, 2H), 3.19-3.23 (m, 2H), 6.79 (d, J = 15.9 Hz, 1H), 7.25-7.30 (m, 2H), 7.42-7.44 (m, 1H), 7.50 (d, J = 15.9 Hz, 1H), 7.64-7.67 (m, 1H), 8.40-8.50 (m, 1H) |
| 14 | 2-F-C6H4-CH=CH-C(O)-NH-(CH2)4-NH2·HCl | Mp. 177-178° C. $^1$H-NMR (DMSO-$d_6$) δ: 1.50-1.54 (m, 2H), 1.56-1.60 (m, 2H), 2.78-2.81 (m, 2H), 3.16-3.21 (m, 2H), 6.77 (d, J = 15.9 Hz, 1H), 7.25-7.31 (m, 2H), 7.43-7.51 (m, 2H), 7.64-7.67 (m, 1H), 8.41 (t, J = 5.6 Hz, 1H) |
| 15 | 2-F-C6H4-CH=CH-C(O)-NH-(CH2)3-(4-methylpiperazin-1-yl)·2HCl | Mp. 133-138° C. $^1$H-NMR (DMSO-$d_6$) δ: 1.91-1.97 (m, 2H), 2.82 (s, 3H), 3.18-3.29 (m, 4H), 3.41-3.78 (m, 8H), 6.75 (d, J = 16.2 Hz, 1H), 7.25-7.30 (m, 2H), 7.42-7.45 (m, 1H), 7.51 (d, J = 16.2 Hz, 1H), 7.64-7.68 (m, 1H), 8.47-8.49 (br, 1H) |

TABLE 2-continued

| Compound No. | Structural Formula | Properties |
|---|---|---|
| 16 | (2-fluorocinnamoyl)-NH-CH2CH2-piperazine · 2HCl | Mp. 212-213° C. $^1$H-NMR (DMSO-$d_6$) δ: 3.31-3.33 (m, 3H), 3.45-3.50 (m, 4H), 3.61-3.64 (m, 3H), 3.70-3.78 (m, 2H), 6.74 (d, J = 15.9 Hz, 1H), 7.26-7.29 (m, 2H), 7.43-7.46 (m, 1H), 7.54 (d, J = 15.9 Hz, 1H), 7.66-7.69 (m, 1H), 8.71 (t, J = 5.2 Hz, 1H), 9.80 (s, 2H) |
| 17 | (2-fluorocinnamoyl)-NH-(CH2)3-piperazine · 2HCl | Mp. 143-144° C. $^1$H-NMR (DMSO-$d_6$) δ: 1.91-1.97 (m, 2H), 3.17-3.21 (m, 2H), 3.26-3.28 (m, 4H), 3.29-3.51 (m, 4H), 3.67-3.69 (m, 2H), 6.76 (d, J = 15.9 Hz, 1H), 7.25-7.30 (m, 2H), 7.42-7.45 (m, 1H), 7.51 (d, J = 15.9 Hz, 1H), 7.65-7.68 (m, 1H), 8.51 (t, J = 5.7 Hz, 1H), 9.78-9.85 (br, 2H) |
| 18 | (2-fluorocinnamoyl)-NH-CH2CH2-(4-imidazolyl) | Mp. 152-153° C. $^1$H-NMR (DMSO-$d_6$) δ: 2.70 (t, J = 7.4 Hz, 2H), 3.38-3.45 (m, 2H), 6.74 (d, J = 15.9 Hz, 1H), 6.83 (s, 1H), 7.25-7.30 (m, 2H), 7.41-7.45 (m, 1H), 7.50 (d, J = 5.9 Hz, 1H), 7.55 (s, 1H), 7.64-7.67 (m, 1H), 8.32 (t, J = 4.7 Hz, 1H) |

TABLE 3

| Compound No. | Structural Formula | Properties |
|---|---|---|
| 19 | (2-fluorocinnamoyl)-NH-CH2CH2-(2-aminophenyl) | Mp. 128-129° C. $^1$H-NMR (DMSO-$d_6$) δ: 2.65 (t, J = 7.8 Hz, 2H), 3.31-3.35 (m, 2H), 5.06 (s, 2H), 6.48 (t, J = 7.5 Hz, 1H), 6.64 (d, J = 7.7 Hz, 1H), 6.76 (d, J = 15.9 Hz, 1H), 6.91-6.94 (m, 2H), 7.25-7.30 (m, 2H), 7.42-7.44 (m, 1H), 7.54 (d, J = 15.9 Hz, 1H), 7.65-7.68 (m, 1H), 8.42 (t, J = 5.6 Hz, 1H) |
| 20 | (2-fluorocinnamoyl)-NH-CH2CH2-(4-methylpiperazine) | Mp. 88-89° C. $^1$H-NMR (DMSO-$d_6$) δ: 1.90-1.92 (m, 2H), 1.96-1.97 (m, 2H), 2.20 (s, 3H), 2.30-2.33 (m, 4H), 3.55-5.57 (m, 2H), 3.67-3.69 (m, 2H), 7.02 (d, J = 15.9 Hz, 1H), 7.24-7.30 (m, 2H), 7.43-7.46 (m, 1H), 7.57-7.62 (m, 2H), 7.95 (t, J = 6.4 Hz, 1H) |
| 21 | (2-fluorocinnamoyl)-NH-CH2CH2-imidazol-1-yl · HCl | $^1$H-NMR (DMSO-$d_6$) δ: 3.50-3.53 (m, 2H), 4.10 (t, J = 5.8 Hz, 2H), 6.71 (d, J = 15.9 Hz, 1H), 6.89 (s, 1H), 7.18 (s, 1H), 7.25-7.30 (m, 2H), 7.42-7.44 (m, 1H), 7.50 (d, J = 15.9 Hz, 1H), 7.60 (s, 1H), 7.64-7.67 (m, 1H), 8.39-8.40 (m, 1H) |
| 22 | (2-fluorocinnamoyl)-NH-CH2CH2-benzimidazol-1-yl | Mp. 143-145° C. $^1$H-NMR (DMSO-$d_6$) δ: 3.61 (t, J = 6.0 Hz, 2H), 4.39 (t, J = 6.0 Hz, 2H), 6.65 (d, J = 15.9 Hz, 1H), 7.18-7.29 (m, 4H), 7.42-7.50 (m, 2H), 7.62-7.65 (m, 3H), 8.39 (s, 1H) |
| 23 | (2,4-difluorocinnamoyl)-NH-CH2CH2-imidazol-1-yl | Mp. 113-115° C. $^1$H-NMR (DMSO-$d_6$) δ: 3.51 (t, J = 6.0 Hz, 2H), 4.10 (t, J = 6.0 Hz, 2H), 6.66 (d, J = 15.9 Hz, 1H), 6.88 (s, 1H), 7.16 (t, J = 6.8 Hz, 2H), 7.32-7.46 (m, 2H), 7.59 (s, 1H), 7.70-7.75 (m, 1H) |

TABLE 3-continued

| Compound No. | Structural Formula | Properties |
|---|---|---|
| 24 | (2,5-difluorocinnamoyl-NH-CH2CH2-imidazole) | Mp. 118-120° C. $^1$H-NMR (DMSO-$d_6$) δ: 3.52 (t, J = 5.9 Hz, 2H), 4.10 (t, J = 5.9 Hz, 2H), 6.74 (d, J = 16.0 Hz, 1H), 6.89 (s, 1H), 7.17 (s, 1H), 7.28-7.36 (m, 3H), 7.44 (d, J = 16.0 Hz, 1H), 7.53 (s, 1H), 7.59 (s, 1H) |
| 25 | (3-fluorocinnamoyl-NH-(CH2)3-morpholine) | Mp. 80-81° C. $^1$H-NMR (DMSO-$d_6$) δ: 1.61-1.63 (m, 2H), 2.29-2.34 (m, 6H), 3.19-3.23 (m, 2H), 3.56-3.58 (m, 4H), 6.66 (d, J = 15.8 Hz, 1H), 7.19-7.22 (m, 1H), 7.40-7.49 (m, 4H), 8.12 (t, J = 5.4 Hz, 1H) |
| 26 | (4-fluorocinnamoyl-NH-(CH2)3-morpholine) | Mp. 88-89° C. $^1$H-NMR (DMSO-$d_6$) δ: 1.59-1.64 (m, 2H), 2.29-2.34 (m, 6H), 3.19-3.21 (m, 2H), 3.56-3.58 (m, 4H), 6.56 (d, J = 15.8 Hz, 1H), 7.23-7.27 (m, 2H), 7.41 (d, J = 15.8 Hz, 1H), 7.61-7.63 (m, 2H), 8.10 (s, 1H). Anal. Calcd for $C_{16}H_{21}FN_2O_2$: C, 65.73; H, 7.24; N, 9.58. Found: C, 65.80; H, 7.20; N, 9.70 |
| 27 | (2,3-difluorocinnamoyl-NH-(CH2)3-morpholine) | Mp. 97-99° C. $^1$H-NMR (DMSO-$d_6$) δ: 1.58-1.65 (m, 2H), 2.27-2.37 (m, 6H), 3.19-3.32 (m, 2H), 3.57 (t, J = 4.6 Hz, 4H), 6.76 (d, J = 16.0 Hz, 1H), 7.24-7.29 (m, 1H), 7.42-7.50 (m, 3H) |

TABLE 4

| Compound No. | Structural Formula | Properties |
|---|---|---|
| 28 | (2,4-difluorocinnamoyl-NH-(CH2)3-morpholine) | Mp. 94-95° C. $^1$H-NMR (DMSO-$d_6$) δ: 1.60-1.65 (m, 2H), 2.29-2.34 (m, 6H), 3.19-3.23 (m, 2H), 3.56-3.58 (m, 4H), 6.68 (d, J = 16.0 Hz, 1H), 7.15-7.18 (m, 1H), 7.32-7.36 (m, 1H), 7.43 (d, J = 16.0 Hz, 1H), 7.70-7.74 (m, 1H), 8.20 (t, J = 4.8 Hz, 1H) |
| 29 | (2,5-difluorocinnamoyl-NH-(CH2)3-morpholine) | Mp. 71-72° C. $^1$H-NMR (DMSO-$d_6$) δ: 1.60-1.65 (m, 2H), 2.29-2.34 (m, 6H), 3.20-3.24 (m, 2H), 3.56-3.58 (m, 4H), 6.76 (d, J = 15.9 Hz, 1H), 7.27-7.36 (m, 2H), 7.43 (d, J = 15.9 Hz, 1H), 7.51-7.53 (m, 1H), 8.24 (s, 1H) |
| 30 | (2,6-difluorocinnamoyl-NH-(CH2)3-morpholine) | Mp. 75-76° C. $^1$H-NMR (DMSO-$d_6$) δ: 1.61-1.64 (m, 2H), 2.29-2.34 (m, 6H), 3.20-3.24 (m, 2H), 3.56-3.58 (m, 4H), 6.86 (d, J = 16.1 Hz, 1H), 7.18-7.22 (m, 2H), 7.43-7.49 (m, 2H), 8.36 (s, 1H) |
| 31 | (3,4-difluorocinnamoyl-NH-(CH2)3-morpholine) | Mp. 127-128° C. $^1$H-NMR (DMSO-$d_6$) δ: 1.60-1.64 (m, 2H), 2.28-2.34 (m, 6H), 3.18-3.22 (m, 2H), 3.56-3.58 (m, 4H), 6.37 (d, J = 15.8 Hz, 1H), 7.37-7.49 (m, 3H), 7.65-7.69 (m, 1H), 8.11 (t, J = 5.3 Hz, 1H) |

TABLE 4-continued

| Compound No. | Structural Formula | Properties |
|---|---|---|
| 32 | (2-F, 4-CF3-phenyl)-CH=CH-C(=O)-NH-(CH2)3-morpholine | Mp. 102-103° C. ¹H-NMR (DMSO-d₆) δ: 1.62-1.65 (m, 2H), 2.30-2.35 (m, 6H), 3.21-3.25 (m, 2H), 3.56-3.59 (m, 4H), 6.86 (d, J = 16.0 Hz, 1H), 7.51 (d, J = 16.0 Hz, 1H), 7.65 (d, J = 8.1 Hz, 1H), 7.77 (d, J = 10.8 Hz, 1H), 7.88-7.91 (m, 1H), 8.35 (t, J = 5.5 Hz, 1H) |
| 33 | (4-F-phenyl)-CH=CH-C(=O)-NH-(4-morpholinophenyl) | Mp. 223-224° C. ¹H-NMR (DMSO-d₆) δ: 3.04-3.07 (m, 4H), 3.73-3.74 (m, 4H), 6.74 (d, J = 15.7 Hz, 1H), 6.92 (d, J = 9.0 Hz, 2H), 7.27-7.30 (m, 2H), 7.53-7.58 (m, 3H), 7.66-7.69 (m, 2H), 10.01 (s, 1H) |
| 34 | (2-F-phenyl)-CH=CH-C(=O)-NH-CH2-CH2-NH2 ·HCl | ¹H-NMR (DMSO-d₆) δ: 2.92-2.94 (m, 2H), 3.43-3.45 (m, 2H), 6.75 (d, J = 16.0 Hz, 1H), 7.24-7.32 (m, 2H), 7.42-7.48 (m, 1H), 7.53 (d, J = 16.0 Hz, 1H), 7.67 (t, J = 7.7 Hz, 1H) |
| 35 | (2-F-phenyl)-CH=CH-C(=O)-NH-CH2-CH2-pyrrolidine | Mp. 83-84° C. ¹H-NMR (CDCl₃) δ: 1.78-1.81 (m, 4H), 2.52-2.54 (m, 4H), 2.66 (t, J = 6.0 Hz, 2H), 3.48-3.52 (m, 2H), 6.32 (s, 1H), 6.57 (d, J = 15.8 Hz, 1H), 7.06-7.15 (m, 2H), 7.29-7.31 (m, 1H), 7.47-7.49 (m, 1H), 7.69 (d, J = 15.8 Hz, 1H) |
| 36 | (2-F-phenyl)-CH=CH-C(=O)-NH-CH2-CH2-azepane | Mp. 80-81° C. ¹H-NMR (DMSO-d₆) δ: 1.62-1.65 (m, 8H), 2.65-2.68 (m, 6H), 3.41-3.45 (m, 2H), 6.41 (s, 1H), 6.56 (d, J = 15.8 Hz, 1H), 7.06-7.15 (m, 2H), 7.29-7.32 (m, 1H), 7.49-7.53 (m, 1H), 7.69 (d, J = 15.8 Hz, 1H) |
| 37 | (2-F-phenyl)-CH=CH-C(=O)-NH-CH2-CH2-(4-OMe-phenyl) | Mp. 123-124° C. ¹H-NMR (DMSO-d₆) δ: 2.72 (t, J = 7.4 Hz, 2H), 3.37-3.41 (m, 2H), 3.72 (s, 3H), 6.73 (d, J = 15.9 Hz, 1H), 6.87 (d, J = 8.5 Hz, 2H), 7.15 (d, J = 8.5 Hz, 2H), 7.24-7.29 (m, 2H), 7.42-7.44 (m, 1H), 7.50 (d, J = 15.9 Hz, 1H), 7.64-7.66 (m, 1H), 8.27 (s, 1H) |

TABLE 5

| Compound No. | Structural Formula | Properties |
|---|---|---|
| 38 | (2-F-phenyl)-CH=CH-C(=O)-NH-CH2-CH2-pyrazol-1-yl | Mp. 124-126° C. ¹H-NMR (DMSO-d₆) δ: 3.57-3.59 (m, 2H), 4.24 (t, J = 6.3 Hz, 2H), 6.23 (s, 1H), 6.70 (d, J = 16.1 Hz, 1H), 7.24-7.29 (m, 2H), 7.42-7.51 (m, 3H), 7.63-7.66 (m, 1H), 7.70 (s, 1H) |
| 39 | (2-F-phenyl)-CH=CH-C(=O)-NH-CH2-CH2-(1,2,4-triazol-1-yl) ·2HCl | ¹H-NMR (DMSO-d₆) δ: 3.61 (t, J = 6.0 Hz, 2H), 4.34 (t, J = 6.0 Hz, 2H), 6.69 (d, J = 15.9 Hz, 1H), 7.24-7.30 (m, 2H), 7.43-7.50 (m, 2H), 7.65 (t, J = 8.9 Hz, 1H), 8.17 (s, 1H), 8.75 (s, 1H) |

TABLE 5-continued

| Compound No. | Structural Formula | Properties |
|---|---|---|
| 40 | 2-fluorocinnamoyl-NH-CH2CH2-(1,2,3-triazol-1-yl) | Mp. 110-112° C. $^1$H-NMR (DMSO-$d_6$) δ: 3.64 (t, J = 6.0 Hz, 2H), 4.52 (t, J = 6.0 Hz, 2H), 6.68 (d, J = 16.0 Hz, 1H), 7.24-7.30 (m, 2H), 7.44-7.51 (m, 2H), 7.64-7.80 (m, 2H), 8.13 (s, 1H) |
| 41 | 2-fluorocinnamoyl-NH-CH2CH2-(indol-1-yl) | Mp. 96-98° C. $^1$H-NMR (DMSO-$d_6$) δ: 3.55 (t, J = 6.1 Hz, 2H), 4.31 (t, J = 6.1 Hz, 2H), 6.43 (s, 1H), 6.67 (d, J = 16.0 Hz, 1H), 7.01-7.14 (m, 2H), 7.24-7.34 (m, 3H), 7.42-7.64 (m, 5H) |
| 42 | 2-fluorocinnamoyl-NH-CH2CH2-(2-methylimidazol-1-yl) | Mp. 127-129° C. $^1$H-NMR (DMSO-$d_6$) δ: 2.25 (s, 3H), 3.44-3.46 (m, 2H), 4.00 (t, J = 6.1 Hz, 2H), 6.69-6.72 (m, 2H), 7.03 (s, 1H), 7.24-7.30 (m, 2H), 7.43-7.65 (m, 3H) |
| 43 | 2-fluorocinnamoyl-NH-CH2CH2-(2-isopropylimidazol-1-yl)·HCl | $^1$H-NMR (DMSO-$d_6$) δ: 1.36 (d, J = 6.9 Hz, 6H), 3.35-3.50 (m, 1H), 3.60-3.70 (m, 2H), 4.31-4.33 (m, 2H), 6.77 (d, J = 16.0 Hz, 1H), 7.26-7.30 (m, 2H), 7.47-7.51 (m, 2H), 7.61-7.70 (m, 3H), 8.84 (s, 1H) |
| 44 | 2-fluorocinnamoyl-NH-CH2CH2-(2-phenylimidazol-1-yl) | Mp. 163-164° C. $^1$H-NMR (DMSO-$d_6$) δ: 3.49-3.53 (m, 2H), 4.17 (t, J = 6.4 Hz, 2H), 6.65 (d, J = 16.0 Hz, 1H), 7.03 (s, 1H), 7.25-7.30 (m, 2H), 7.33 (s, 1H), 7.40-7.48 (m, 5H), 7.61-7.66 (m, 3H), 8.40 (t, J = 5.6 Hz, 1H) |
| 45 | 2-fluorocinnamoyl-NH-(CH2)3-(imidazol-1-yl)·HCl | $^1$H-NMR (DMSO-$d_6$) δ: 1.89-1.91 (m, 2H), 3.13-3.18 (m, 2H), 4.00 (t, J = 6.9 Hz, 2H), 6.72 (d, J = 16.0 Hz, 1H), 6.89 (s, 1H), 7.20 (s, 1H), 7.25-7.30 (m, 2H), 7.43-7.44 (m, 1H), 7.50 (d, J = 16.0 Hz, 1H), 7.64-7.66 (m, 2H) |
| 46 | 4-fluoro-α-methylcinnamoyl-NH-(CH2)3-morpholino | Mp. 78-79° C. $^1$H-NMR (DMSO-$d_6$) δ: 1.62-1.65 (m, 2H), 1.99 (s, 3H), 2.30-2.35 (m, 6H), 3.19-3.20 (m, 2H), 3.55-3.58 (m, 4H), 7.18 (s, 1H), 7.23-7.26 (m, 2H), 7.43-7.45 (m, 2H), 8.07 (t, J = 5.2 Hz, 1H) |
| 47 | 2-carboxycinnamoyl-NH-CH2CH2-(imidazol-1-yl) | $^1$H-NMR (DMSO-$d_6$) δ: 3.50-3.54 (m, 2H), 4.12 (t, J = 6.0 Hz, 2H), 6.51 (d, J = 15.8 Hz, 1H), 6.94 (s, 1H), 7.21 (s, 1H), 7.45-7.48 (m, 1H), 7.57-7.60 (m, 1H), 7.64-7.69 (m, 2H), 7.85 (d, J = 7.8 Hz, 1H), 8.14 (d, J = 15.8 Hz, 1H), 8.31 (t, J = 5.1 Hz, 1H) |

TABLE 6

| Compound No. | Structural Formula | Properties |
|---|---|---|
| 48 | 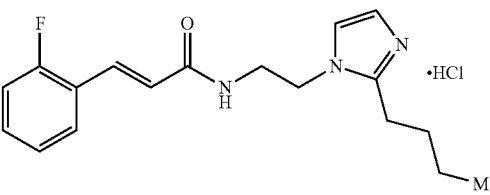 | $^1$H-NMR (DMSO-d$_6$) δ: 0.85 (t, J = 7.3 Hz, 3H), 1.30-1.38 (m, 2H), 1.67-1.78 (m, 2H), 2.96 (t, J = 7.8 Hz, 2H), 3.60-3.68 (m, 2H), 4.30-4.38 (m, 2H), 6.77 (d, J = 16.0 Hz, 1H), 7.26-7.30 (m, 2H), 7.40-7.51 (m, 2H), 7.59 (s, 1H), 7.60-7.70 (m, 1H), 7.73 (s, 1H), 8.84 (s, 1H) |
| 49 | 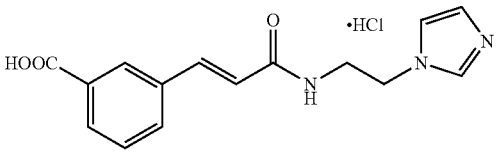 [SMILES: O=C(/C=C/c1cccc(C(=O)O)c1)NCCn1ccnc1 ; Cl] | Mp. 195-197° C. $^1$H-NMR (DMSO-d$_6$) δ: 3.50-3.54 (m, 2H), 4.10-4.14 (m, 2H), 6.80 (d, J = 16.0 Hz, 1H), 6.88 (s, 1H), 7.20 (s, 1H), 7.46 (d, J = 16.0 Hz, 1H), 7.63-7.66 (m, 3H), 7.94-7.96 (m, 2H) |
| 50 | 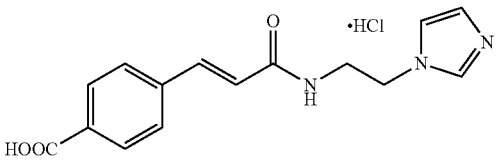 [SMILES: O=C(/C=C/c1ccc(C(=O)O)cc1)NCCn1ccnc1 ; Cl] | Mp. 237-238° C. $^1$H-NMR (DMSO-d$_6$) δ: 3.62-3.69 (m, 2H), 4.33-4.40 (m, 2H), 6.80 (d, J = 16.0 Hz, 1H), 7.46 (d, J = 16.0 Hz, 1H), 7.66-7.68 (m, 3H), 7.83 (s, 1H), 7.94-7.96 (m, 2H), 9.26 (s, 1H) |
| 51 | 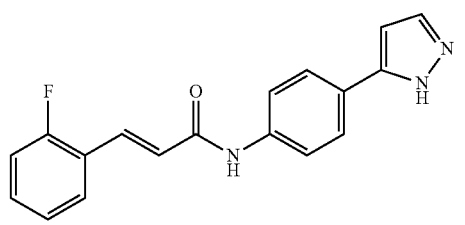 [SMILES: O=C(/C=C/c1ccccc1F)Nc1ccc(-c2ccn[nH]2)cc1] | Mp. 116-118° C. $^1$H-NMR (DMSO-d$_6$) δ: 6.65 (m, 1H), 6.98 (d, J = 16.0 Hz, 1H), 7.31-7.80 (m, 9H), 8.17 (s, 1H) |
| 52 | 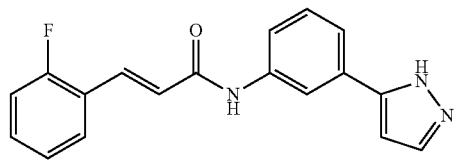 | $^1$H-NMR (DMSO-d$_6$) δ: 6.66 (m, 1H), 6.98 (d, J = 16.0 Hz, 1H), 7.31-7.80 (m, 9H), 8.17 (s, 1H) |
| 53 | 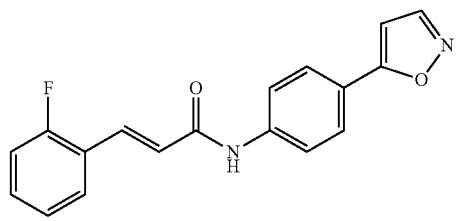 [SMILES: O=C(/C=C/c1ccccc1F)Nc1ccc(-c2ccno2)cc1] | Mp. 204-206° C. $^1$H-NMR (DMSO-d$_6$) δ: 6.94-6.99 (m, 2H), 7.30-7.34 (m, 2H), 7.48-7.50 (m, 1H), 7.66 (s, 1H), 7.70-7.44 (m, 2H), 7.88 (s, 4H), 8.63 (s, 1H) |
| 54 | 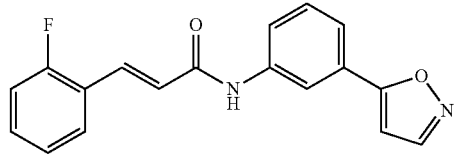 [SMILES: O=C(/C=C/c1ccccc1F)Nc1cccc(-c2ccno2)c1] | Mp. 185-187° C. $^1$H-NMR (DMSO-d$_6$) δ: 6.95-7.00 (m, 2H), 7.30-7.34 (m, 2H), 7.53-7.61 (m, 2H), 7.67-7.80 (m, 4H), 8.29 (s, 1H), 8.68 (s, 1H) |
| 55 | 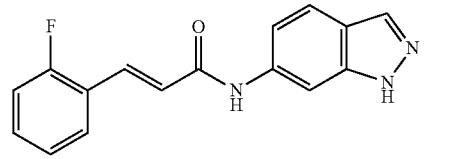 [SMILES: O=C(/C=C/c1ccccc1F)Nc1ccc2cn[nH]c2c1] | $^1$H-NMR (DMSO-d$_6$) δ: 7.00 (d, J = 16.0 Hz, 1H), 7.16-7.18 (m, 1H), 7.29-7.36 (m, 2H), 7.45-7.51 (m, 1H), 7.64-7.76 (m, 3H), 7.99 (s, 1H), 8.33 (s, 1H) |

TABLE 6-continued

| Compound No. | Structural Formula | Properties |
|---|---|---|
| 56 | (2-fluorophenyl)-CH=CH-C(=O)-NH-(1H-indazol-5-yl) | ¹H-NMR (DMSO-d₆) δ: 6.98 (d, J = 16.0 Hz, 1H), 7.29-7.35 (m, 2H), 7.44-7.53 (m, 2H), 7.62-7.75 (m, 2H), 8.05 (s, 1H), 8.29 (s, 1H) |
| 57 | (2-trifluoromethylphenyl)-CH=CH-C(=O)-NH-(CH₂)₃-morpholine · HCl | Mp. 197-198° C. ¹H-NMR (DMSO-d₆) δ: 1.97-1.99 (m, 2H), 3.04-3.14 (m, 4H), 3.26-3.30 (m, 2H), 3.38-3.42 (m, 2H), 3.81-3.86 (m, 2H), 3.94-3.96 (m, 2H), 6.77 (d, J = 15.5 Hz, 1H), 7.61-7.62 (m, 1H), 7.70-7.85 (m, 4H), 8.65 (t, J = 5.5 Hz, 1H), 11.19 (s,1H) |

TABLE 7

| Compound No. | Structural Formula | Properties |
|---|---|---|
| 58 | (4-fluorophenyl)-CH=C(CN)-C(=O)-NH-(CH₂)₃-morpholine | Mp. 110-111° C. ¹H-NMR (DMSO-d₆) δ: 1.65-1.68 (m, 2H), 2.31-2.35 (m, 6H), 3.27-3.29 (m, 2H), 3.57-3.59 (m, 4H), 7.42-7.45 (m, 2H), 8.03-8.06 (m, 2H), 8.19 (s, 1H), 8.47 (s, 1H) |
| 59 | (2-fluorophenyl)-CH=CH-C(=O)-NH-(CH₂)₃-piperidine · HCl | Mp. 166-167° C. ¹H-NMR (DMSO-d₆) δ: 1.33-1.40 (m, 1H), 1.68-1.96 (m, 7H), 2.80-2.87 (m, 2H), 3.01-3.05 (m, 2H), 3.24-3.28 (m, 2H), 3.38-3.40 (m, 2H), 6.78 (d, J = 15.9 Hz, 1H), 7.26-7.31 (m, 2H), 7.42-7.46 (m, 1H), 7.51 (d, J = 15.9 Hz, 1H), 7.65-7.68 (m, 1H), 8.59 (d, J = 5.3Hz, 1H), 10.45 (s, 1H) |
| 60 | (4-fluorophenyl)-CH=CH-C(=O)-NH-(CH₂)₃-thiomorpholine | Mp. 121-122° C. MS (EI) m/z: 308 (M⁺). ¹H-NMR (DMSO-d₆) δ: 1.57-1.63 (m, 2H), 2.32-2.34 (m, 2H), 2.57-2.59 (m, 8H), 3.16-3.20 (m, 2H), 6.56 (d, J = 15.8 Hz, 1H), 7.23-7.27 (m, 2H), 7.41 (d, J = 15.8 Hz, 1H), 7.60-7.63 (m, 2H), 8.09 (s, 1H) |
| 61 | (2-fluorophenyl)-CH=CH-C(=O)-NH-(CH₂)₃-thiomorpholine · HCl | Mp. 178-179° C. ¹H-NMR (DMSO-d₆) δ: 1.92-1.98 (m, 2H), 2.78-2.81 (m, 2H), 3.07-3.13 (m, 4H), 3.24-3.29 (m, 2H), 3.67-3.70 (m, 2H), 6.77 (d, J = 16.0 Hz, 1H), 7.26-7.31 (m, 2H), 7.43-7.52 (m, 2H), 7.65-7.68 (m, 1H), 8.56 (t, J = 5.6 Hz, 1H), 11.17 (s, 1H) |
| 62 | (2-fluorophenyl)-CH=CH-C(=O)-NH-(CH₂)₃-thiomorpholine-1,1-dioxide · HCl | Mp. 252-253° C. ¹H-NMR (DMSO-d₆) δ: 1.96-1.98 (m, 2H), 3.26-3.28 (m, 4H), 3.57-3.62 (m, 4H), 3.87-3.89 (m, 4H), 6.77 (d, J = 15.9 Hz, 1H), 7.26-7.31 (m, 2H), 7.44-7.53 (m, 2H), 7.65-7.68 (m, 1H), 8.55 (s, 1H), 12.00-12.20 (br, 1H) |
| 63 | (4-fluorophenyl)-CH=CH-C(=O)-NH-(CH₂)₃-thiomorpholine-1,1-dioxide · HCl | Mp. 247-248° C. ¹H-NMR (DMSO-d₆) δ: 1.93-1.99 (m, 2H), 3.24-3.29 (m, 4H), 3.57-3.61 (m, 4H), 3.86-3.88 (m, 4H), 6.62 (d, J = 15.8 Hz, 1H), 7.24-7.28 (m, 2H), 7.44 (d, J = 15.8 Hz, 1H), 7.63-7.65 (m, 2H), 8.44 (t, J = 5.6 Hz, 1H), 12.00-12.25 (br, 1H) |

TABLE 7-continued

| Compound No. | Structural Formula | Properties |
|---|---|---|
| 64 | 2-F-C6H4-CH=CH-C(O)-NH-(CH2)3-NH-cyclohexyl · HCl | Mp. 227-228° C. $^1$H-NMR (DMSO-$d_6$) δ: 1.08-1.38 (m, 5H), 1.59-1.61 (m, 1H), 1.74-1.77 (m, 2H), 1.83-1.89 (m, 2H), 2.03-2.05 (m, 2H), 2.90-2.93 (m, 3H), 3.25-3.29 (m, 2H), 6.77 (d, J = 16.0 Hz, 1H), 7.25-7.31 (m, 2H), 7.43-7.45 (m, 1H), 7.51 (d, J = 16.0 Hz, 1H), 7.65-7.68 (m, 1H), 8.57 (t, J = 5.7 Hz, 1H), 8.93 (s, 2H) |
| 65 | 2-F-C6H4-CH=CH-C(O)-NH-(CH2)4-NH-C(=NH)NH2 · HCl | Mp. 154-156° C. $^1$H-NMR (DMSO-$d_6$) δ: 1.50 (m, 4H), 3.14 (m, 2H), 3.20 (m, 2H), 6.79 (d, J = 16.0 Hz, 1H), 7.26-7.28 (m, 2H), 7.42-7.51 (m, 2H), 7.65 (t, J = 7.7 Hz, 1H) |
| 66 | 2-F-C6H4-CH=CH-C(O)-NH-CH2CH2-COOH | Mp. 193-195° C. $^1$H-NMR (DMSO-$d_6$) δ: 2.18 (t, J = 7.0 Hz, 2H), 3.33 (t, J = 7.0 Hz, 2H), 6.78 (d, J = 16.0 Hz, 1H), 7.23-7.28 (m, 2H), 7.41-7.48 (m, 2H), 7.66 (t, J = 7.5 Hz, 1H) |

TABLE 8

| Compound No. | Structural Formula | Properties |
|---|---|---|
| 67 | 4-F-C6H4-CH=CH-C(O)-NH-(CH2)3-N(thiomorpholine-S-oxide) | Mp. 130-131° C. MS (EI) m/z: 324 [M$^+$]. $^1$H-NMR (DMSO-$d_6$) δ: 1.61-1.64 (m, 2H), 2.39 (t, J = 7.0 Hz, 2H), 2.61-2.64 (m, 2H), 2.71-2.74 (m, 2H), 2.81-2.87 (m, 4H), 3.18-3.22 (m, 2H), 6.57 (d, J = 15.8 Hz, 1H), 7.23-7.27 (m, 2H), 7.42 (d, J = 15.8 Hz, 1H), 7.61-7.64 (m, 2H), 8.09 (t, J = 5.5 Hz, 1H) |
| 68 | 2-F-C6H4-CH=CH-C(O)-NH-(CH2)3-N(thiomorpholine-S-oxide) · HCl | Mp. 182-183° C. MS (EI) m/z: 324 [M$^+$]. (free form). $^1$H-NMR (DMSO-$d_6$) δ: 1.97-2.00 (m, 2H), 3.14-3.36 (m, 8H), 3.55-3.61 (m, 4H), 6.77 (d, J = 16.0 Hz, 1H), 7.25-7.31 (m, 2H), 7.41-7.46 (m, 1H), 7.51 (d, J = 16.0 Hz, 1H), 7.65-7.68 (m, 1H), 7.54 (t, J = 5.6 Hz, 1H), 11.57 (s, 1H) |
| 69 | 2-F-C6H4-CH=CH-C(O)-NH-CH2-(3-thiomorpholin-4-yl-phenyl) | Mp. 154-155° C. MS (EI) m/z: 356 [M$^+$]. $^1$H-NMR (DMSO-$d_6$) δ: 2.65-2.67 (m, 4H), 3.50-3.52 (m, 4H), 4.35 (d, J = 5.9 Hz, 2H), 6.72 (d, J = 7.5 Hz, 1H), 6.79-6.83 (m, 2H), 6.87 (s, 1H), 7.16-7.19 (m, 1H), 7.25-7.30 (m, 2H), 7.41-7.44 (m, 1H), 7.54 (d, J = 16.0 Hz, 1H), 7.64-7.68 (m, 1H), 8.65 (t, J = 5.8 Hz, 1H) |
| 70 | 2-F-C6H4-CH=CH-C(O)-NH-CH2-(3-(thiomorpholine-S-oxide-4-yl)-phenyl) | Mp. 156-157° C. MS (EI) m/z: 372 [M$^+$]. $^1$H-NMR (DMSO-$d_6$) δ: 2.68-2.71 (m, 2H), 2.90-2.94 (m, 2H), 3.57-3.60 (m, 2H), 3.74-3.79 (m, 2H), 4.37 (d, J = 4.6 Hz, 2H), 6.79-6.82 (m, 2H), 6.90-6.96 (m, 2H), 7.19-7.30 (m, 3H), 7.43-7.44 (m, 1H), 7.54 (d, J = 15.9 Hz, 1H), 7.66 (t, J = 6.5 Hz, 1H), 8.66 (s, 1H) |
| 71 | 2-F-C6H4-CH=C(Me)-C(O)-NH-(CH2)3-N(thiomorpholine-S-oxide) · HCl | Mp. 180-181° C. MS (EI) m/z: 338 [M$^+$]. (free form). $^1$H-NMR (DMSO-$d_6$) δ: 1.95-2.03 (m, 5H), 3.15-3.37 (m, 6H), 3.56-3.65 (m, 4H), 3.72-3.77 (m, 2H), 7.25-7.28 (m, 3H), 7.39-7.44 (m, 2H), 8.30 (t, J = 5.6 Hz, 1H), 11.52 (s, 1H) |

Example 113

Analgesic Efficacy Test (1)

A compound of the present invention was orally administered to mice, to carry out an analgesic efficacy test according to acetic acid writhing test. As an experimental animal, 4-week old male ddY-type mice were previously bred, and thereafter 8 mice per one group were used in the experiment. A solution or suspension prepared by dissolving or suspending a compound of the present invention in a 0.5% (w/v) aqueous CMC-Na solution was orally administered as a test substance in a single dose. While, to a control group, a 0.5% (w/v) aqueous CMC-Na solution was administered in the same manner After 25 minutes from administration, the mice were intraperitoneally administered with a 0.7% (v/v) acetic acid/physiological saline at the dose of 10 mL/kg. From 5 minutes thereafter, writhing number in a 10-minute period was counted, and a suppressive rate for each individual (mean±standard error) was calculated by the following formula:

$$\text{Suppressive Rate}(\%) = \frac{\text{Mean Writhing Number of Control Group} - \text{Writhing Number of Each Individual}}{\text{Mean Writhing Number of Control Group}} \times 100$$

In the test for significance difference, Bartlett's test was carried out in the comparison between multiple groups of the group administered with test substance with the control group. In the case of homoscedasticity, Dunnett's multiple comparison test of parametrics, and in the case of heteroscedasticity, Dunnett's multiple comparison test of non-parametrics were used. In addition, in the test of dose dependency, Jonckheere-Terpstra's test was used. In all cases, significance difference was considered to be found at $P<0.05$ (indicated as "*" in the table).

One example of the above test results is shown in Table 9. As a result of conducting the analgesic efficacy test according to acetic acid writhing test, the compounds of the present invention exhibited excellent analgesic effects.

TABLE 9

| Test Substance | Dose of Test Substance (mg/kg) | Suppressive Rate (%) |
|---|---|---|
| Compound 1 | 10 | 46.9 ± 7.6* |
| | 100 | 62.7 ± 6.0* |
| Compound 2 | 10 | 39.9 ± 10.4* |
| | 100 | 39.9 ± 10.0* |
| Compound 3 | 10 | 44.4 ± 11.1* |
| | 100 | 59.0 ± 8.1* |
| Compound 4 | 10 | 47.0 ± 7.8* |
| | 100 | 49.0 ± 9.2* |
| Compound 5 | 10 | 34.8 ± 10.3 |
| | 100 | 95.7 ± 3.1* |
| Compound 6 | 10 | 29.6 ± 12.8 |
| | 100 | 70.4 ± 6.1* |
| Compound 7 | 10 | 41.5 ± 17.2 |
| | 100 | 68.4 ± 8.0* |
| Compound 8 | 10 | 8.5 ± 13.9 |
| | 100 | 28.1 ± 8.3 |
| Compound 11 | 10 | 23.2 ± 12.8 |
| | 100 | 68.9 ± 4.5* |
| Compound 12 | 10 | −4.3 ± 12.0 |
| | 100 | 49.4 ± 14.5* |

TABLE 9-continued

| Test Substance | Dose of Test Substance (mg/kg) | Suppressive Rate (%) |
|---|---|---|
| Compound 14 | 10 | 46.3 ± 11.1 |
| | 100 | 76.8 ± 4.1* |
| Compound 15 | 10 | 24.3 ± 12.7 |
| | 100 | 44.1 ± 6.6* |
| Compound 16 | 10 | 42.6 ± 9.1* |
| | 100 | 65.5 ± 8.9* |
| Compound 18 | 10 | 54.3 ± 13.2* |
| | 100 | 62.3 ± 14.6* |
| Compound 21 | 10 | 44.5 ± 11.7* |
| | 100 | 49.7 ± 4.7* |

Example 114

Analgesic Efficacy Test (2)

An analgesic efficacy test was conducted using a Chung model rat, a neuropathic pain model. Nine-week old Wistar male rats were previously bred as an experimental animal, and a model rat was then prepared in accordance with the method of Kim and Chung (*Pain*, 50, 355-363, 1992). Specifically, left L5 spinal nerves of rats were exposed under anesthetization with pentobarbital (40 mg/kg, intraperitoneal administration), and firmly ligated with 5-0 silk yarn at L5 dorsal root ganglion peripheral side. The animals were placed in a transparent acrylic cage of which bottom was wire netted The measurement of allodynia was carried out using von Frey filament (manufactured by North Coast Medical Inc.) and a 50% reaction threshold was calculated according to an up-down method, in accordance with a method of Chaplan et al. (*J. Neurosci. Method*, 53, 55-63, 1994). The 50% reaction thresholds were measured twice before injury of the spinal nerve, and those animals of which thresholds were outside the standard were removed from the operation of spinal nerve injury. On or after 14 days from the spinal nerve injury, a 50% reaction threshold was measured, and those showing thresholds of 1 g or more and less than 4 g were used as experimental animal. The group was constituted by 7 or 8 rats per group so that an average of a 50% reaction threshold for each group would be nearly even.

A solution or suspension prepared by dissolving or suspending a compound of the present invention in a 0.5% (w/v) aqueous CMC-Na solution was orally administered as a test substance in a single dose. Also, a 0.5% (w/v) aqueous CMC-Na solution was administered in the same manner to the control group for nerve injury. The measurements of allodynia were carried out with the passage of time after administration, and a 50% reaction threshold (mean±standard error) of each group at action peak was calculated. In the test for significance difference, Bartlett's test was carried out in the comparison between multiple groups of the group administered with test substance with the control group for nerve injury. In the case of homoscedasticity, Dunnett's multiple comparison test of parametrics, and in the case of heteroscedasticity, Dunnett's multiple comparison test of non-parametrics were used. In all cases, significance difference was considered to be found at $P<0.05$ (indicated as "*" in the tables).

One example of the above test results is shown in Tables 10 to 12. As a result of conducting the analgesic efficacy test using Chung model rats, a neuropathic pain model, the compounds of the present invention exhibited significantly excellent analgesic effects.

TABLE 10

| Test Substance | Dose of Test Substance (mg/kg) | Measurement Point (minute) | 50% Reaction Threshold (g) | | | |
|---|---|---|---|---|---|---|
| | | | Control Group for Nerve Injury | | Group Administered with Test Substance | |
| | | | Before Administration | After Administration | Before Administration | After Administration |
| Compound 1 | 1 | 90 | 2.79 ± 0.22 | 3.13 ± 0.22 | 2.79 ± 0.08 | 6.71 ± 1.33 |
| | 10 | | | | 2.74 ± 0.06 | 14.06 ± 0.61* |
| Compound 2 | 1 | 30 | 2.85 ± 0.21 | 3.51 ± 0.30 | 2.87 ± 0.15 | 4.85 ± 0.78 |
| | 10 | | | | 2.84 ± 0.16 | 7.76 ± 1.30* |
| Compound 3 | 1 | 90 | 2.81 ± 0.00 | 3.32 ± 0.39 | 2.79 ± 0.08 | 6.74 ± 1.04* |
| | 10 | | | | 2.81 ± 0.00 | 10.06 ± 1.60* |
| Compound 4 | 1 | 30 | 2.75 ± 0.23 | 3.08 ± 0.33 | 2.74 ± 0.06 | 3.98 ± 0.21 |
| | 10 | | | | 2.74 ± 0.06 | 7.35 ± 0.95* |
| Compound 5 | 1 | 90 | 2.69 ± 0.11 | 2.97 ± 0.32 | 2.98 ± 0.13 | 4.91 ± 0.73 |
| | 10 | | | | 2.98 ± 0.13 | 8.68 ± 1.91* |
| Compound 6 | 1 | 90 | 2.68 ± 0.08 | 3.92 ± 0.39 | 2.69 ± 0.12 | 10.87 ± 1.24* |
| | 10 | | | | 2.74 ± 0.06 | 14.06 ± 0.61* |
| Compound 7 | 1 | 90 | 2.68 ± 0.08 | 3.92 ± 0.39 | 2.69 ± 0.12 | 9.05 ± 1.80 |
| | 10 | | | | 2.72 ± 0.06 | 12.70 ± 1.16* |
| Compound 8 | 1 | 90 | 2.96 ± 0.11 | 2.97 ± 0.32 | 2.94 ± 0.13 | 4.37 ± 0.53 |
| | 10 | | | | 2.96 ± 0.15 | 5.57 ± 1.18* |
| Compound 11 | 1 | 60 | 2.69 ± 0.24 | 3.41 ± 0.22 | 2.63 ± 0.18 | 11.69 ± 1.80* |
| | 10 | | | | 2.67 ± 0.14 | 14.27 ± 0.73* |
| Compound 12 | 1 | 60 | 2.85 ± 0.21 | 3.60 ± 0.51 | 2.87 ± 0.15 | 4.64 ± 0.70 |
| | 10 | | | | 2.87 ± 0.15 | 5.00 ± 1.17 |
| Compound 14 | 1 | 60 | 2.69 ± 0.24 | 3.41 ± 0.22 | 2.63 ± 0.18 | 12.38 ± 1.15* |
| | 10 | | | | 2.74 ± 0.23 | 13.61 ± 0.96* |
| Compound 15 | 1 | 90 | 2.85 ± 0.21 | 3.50 ± 0.23 | 2.82 ± 0.19 | 7.45 ± 1.95* |
| | 10 | | | | 2.85 ± 0.05 | 7.43 ± 1.63* |
| Compound 16 | 1 | 90 | 2.68 ± 0.08 | 3.92 ± 0.39 | 2.67 ± 0.14 | 5.48 ± 0.82 |
| | 10 | | | | 2.67 ± 0.14 | 7.48 ± 1.30 |
| Compound 18 | 1 | 90 | 2.69 ± 0.11 | 2.97 ± 0.32 | 2.94 ± 0.13 | 10.92 ± 1.33* |
| | 10 | | | | 2.94 ± 0.13 | 11.44 ± 1.95* |
| Compound 21 | 0.1 | 90 | 2.81 ± 0.00 | 3.72 ± 0.22 | 2.81 ± 0.00 | 6.04 ± 0.89 |
| | 0.3 | | | | 2.81 ± 0.00 | 8.80 ± 1.42* |
| | 1 | | | | 2.81 ± 0.00 | 11.78 ± 1.20* |

TABLE 11

| Test Substance | Dose of Test Substance (mg/kg) | Measurement Point (minute) | 50% Reaction Threshold (g) | | | |
|---|---|---|---|---|---|---|
| | | | Control Group for Nerve Injury | | Group Administered with Test Substance | |
| | | | Before Administration | After Administration | Before Administration | After Administration |
| Compound 23 | 1 | 90 | 2.74 ± 0.06 | 3.48 ± 0.40 | 2.74 ± 0.06 | 8.22 ± 1.43* |
| | 10 | | | | 2.74 ± 0.06 | 9.81 ± 1.27* |
| Compound 24 | 1 | 60 | 2.74 ± 0.06 | 3.12 ± 0.27 | 2.74 ± 0.06 | 4.63 ± 0.36 |
| | 10 | | | | 2.74 ± 0.06 | 7.85 ± 0.99* |
| Compound 25 | 1 | 60 | 2.81 ± 0.00 | 2.68 ± 0.34 | 2.81 ± 0.00 | 8.17 ± 1.09* |
| | 10 | | | | 2.81 ± 0.00 | 9.68 ± 1.20* |
| Compound 26 | 1 | 60 | 2.74 ± 0.13 | 3.19 ± 0.27 | 2.74 ± 0.06 | 10.25 ± 1.07* |
| | 10 | | | | 2.74 ± 0.06 | 14.33 ± 0.67* |
| Compound 28 | 1 | 60 | 2.74 ± 0.13 | 3.19 ± 0.27 | 2.81 ± 0.00 | 8.44 ± 1.81* |
| | 10 | | | | 2.81 ± 0.00 | 12.05 ± 1.44* |
| Compound 29 | 1 | 60 | 2.81 ± 0.00 | 2.68 ± 0.34 | 2.81 ± 0.00 | 5.10 ± 0.42 |
| | 10 | | | | 2.81 ± 0.00 | 10.51 ± 1.15* |
| Compound 33 | 1 | 60 | 2.74 ± 0.06 | 3.12 ± 0.31 | 2.81 ± 0.00 | 8.93 ± 1.46* |
| | 10 | | | | 2.81 ± 0.00 | 9.35 ± 2.10* |
| Compound 38 | 1 | 90 | 2.77 ± 0.11 | 2.45 ± 0.17 | 2.74 ± 0.06 | 2.74 ± 0.23 |
| | 10 | | | | 2.81 ± 0.00 | 4.06 ± 0.52* |
| Compound 39 | 1 | 90 | 2.77 ± 0.11 | 2.45 ± 0.17 | 2.81 ± 0.00 | 3.55 ± 0.59 |
| | 10 | | | | 2.81 ± 0.00 | 4.05 ± 0.48* |
| Compound 40 | 1 | 60 | 2.79 ± 0.08 | 3.07 ± 0.25 | 2.81 ± 0.00 | 3.61 ± 0.41 |
| | 10 | | | | 2.81 ± 0.00 | 5.86 ± 1.17* |

TABLE 11-continued

| Test Substance | Dose of Test Substance (mg/kg) | Measurement Point (minute) | 50% Reaction Threshold (g) | | | |
|---|---|---|---|---|---|---|
| | | | Control Group for Nerve Injury | | Group Administered with Test Substance | |
| | | | Before Administration | After Administration | Before Administration | After Administration |
| Compound 42 | 1 | 30 | 2.77 ± 0.11 | 2.68 ± 0.08 | 2.81 ± 0.00 | 2.60 ± 0.32 |
| | 10 | | | | 2.81 ± 0.00 | 4.24 ± 0.35* |
| Compound 45 | 1 | 90 | 2.74 ± 0.13 | 3.39 ± 0.25 | 2.81 ± 0.00 | 8.81 ± 1.05* |
| | 10 | | | | 2.81 ± 0.00 | 12.23 ± 1.10* |
| Compound 46 | 1 | 30 | 2.74 ± 0.06 | 2.58 ± 0.20 | 2.81 ± 0.00 | 7.51 ± 1.60* |
| | 10 | | | | 2.81 ± 0.00 | 8.70 ± 1.43* |
| Compound 47 | 1 | 60 | 2.74 ± 0.06 | 3.12 ± 0.27 | 2.81 ± 0.00 | 10.58 ± 1.74* |
| | 10 | | | | 2.81 ± 0.00 | 13.58 ± 0.67* |
| Compound 52 | 1 | 30 | 2.75 ± 0.23 | 2.93 ± 0.33 | 2.63 ± 0.18 | 7.42 ± 1.14* |
| | 10 | | | | 2.67 ± 0.14 | 9.12 ± 2.00* |

TABLE 12

| Test Substance | Dose of Test Substance (mg/kg) | Measurement Point (minute) | 50% Reaction Threshold (g) | | | |
|---|---|---|---|---|---|---|
| | | | Control Group for Nerve Injury | | Group Administered with Test Substance | |
| | | | Before Administration | After Administration | Before Administration | After Administration |
| Compound 54 | 1 | 30 | 2.75 ± 0.23 | 2.93 ± 0.33 | 2.67 ± 0.14 | 5.18 ± 0.81 |
| | 10 | | | | 2.74 ± 0.17 | 11.20 ± 1.19* |
| Compound 60 | 1 | 30 | 2.72 ± 0.15 | 3.02 ± 0.44 | 2.72 ± 0.09 | 4.03 ± 0.54 |
| | 10 | | | | 2.72 ± 0.09 | 8.45 ± 1.01* |
| Compound 61 | 1 | 60 | 2.79 ± 0.22 | 2.86 ± 0.28 | 2.74 ± 0.06 | 10.64 ± 1.38* |
| | 10 | | | | 2.72 ± 0.09 | 11.81 ± 1.47* |
| Compound 62 | 1 | 90 | 2.63 ± 0.25 | 3.23 ± 0.37 | 2.66 ± 0.25 | 6.17 ± 1.33 |
| | 10 | | | | 2.68 ± 0.23 | 9.22 ± 1.28* |
| Compound 63 | 1 | 90 | 2.72 ± 0.15 | 3.30 ± 0.30 | 2.74 ± 0.06 | 3.60 ± 0.35 |
| | 10 | | | | 2.78 ± 0.02 | 6.74 ± 0.62* |
| Compound 65 | 1 | 60 | 2.74 ± 0.06 | 3.12 ± 0.41 | 2.74 ± 0.06 | 5.01 ± 0.52* |
| | 10 | | | | 2.81 ± 0.00 | 5.24 ± 0.47* |
| Compound 67 | 1 | 60 | 2.75 ± 0.23 | 3.14 ± 0.22 | 2.72 ± 0.09 | 10.63 ± 1.23* |
| | 10 | | | | 2.68 ± 0.08 | 10.71 ± 2.13* |
| Compound 68 | 1 | 90 | 2.63 ± 0.25 | 3.23 ± 0.37 | 2.68 ± 0.23 | 9.04 ± 1.17* |
| | 10 | | | | 2.60 ± 0.13 | 11.25 ± 0.94* |
| Compound 69 | 1 | 60 | 2.62 ± 0.29 | 2.30 ± 0.26 | 2.59 ± 0.21 | 3.68 ± 0.40* |
| | 10 | | | | 2.61 ± 0.20 | 4.35 ± 0.51* |
| Compound 70 | 1 | 60 | 2.62 ± 0.29 | 2.30 ± 0.26 | 2.61 ± 0.14 | 4.09 ± 0.34* |
| | 10 | | | | 2.63 ± 0.18 | 3.41 ± 0.31* |

INDUSTRIAL APPLICABILITY

As shown in various analgesic effect tests described above, the cinnamic acid amide derivative of the present invention is a compound that shows an excellent analgesic action to not only a model animal for nociceptive pains but also a model animal for neuropathic pains, and also has excellent migration into the blood upon the oral administration. Therefore, the compound of the present invention is very useful as a drug for treating various acute or chronic pain diseases and neuropathic pain diseases such as reflex sympathetic dystrophy, postherpetic neuralgia or diabetic neuropathy for which analgesics such as nonsteroidal anti-inflammatory drugs (NSAIDs) are less likely to effect.

The invention claimed is:

1. A compound of formula (I):

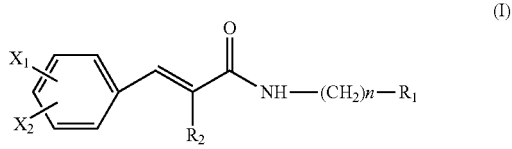

(I)

or a pharmaceutically acceptable salt or hydrate thereof, where:

n is 1, 2, 3, or 4;

each of $X_1$ and $X_2$ is independently selected from the group consisting of hydrogen, fluoro, trifluoromethyl, and carboxy, with the proviso that one of $X_1$ and $X_2$ is selected from the group consisting of fluoro, trifluoromethyl, and carboxy;

$R_1$ is selected from the group consisting of:
(1) imidazolyl, substituted with alkyl having 3 to 6 carbon atoms or phenyl;
(2) pyrrolyl, optionally substituted with alkyl having 1 to 4 carbon atoms;
(3) phenyl, substituted with amino, isoxazolyl, or morpholino;
(4) phenyl, substituted with thiomorpholino, optionally substituted with oxo;
(5) piperazine, substituted with alkyl having 1 to 4 carbon atoms or cyclohexyl;
(6) thiomorpholino, optionally substituted with one or two oxos;
(7) indazolyl; and
(8) cyclohexylamino; and $R_2$ is selected from the group consisting of hydrogen, cyano, and alkyl having 1 to 4 carbon atoms.

2. The compound according to claim 1, or a pharmaceutically acceptable salt or hydrate thereof, where:
one of $X_1$ and $X_2$ is hydrogen, and the other of $X_1$ and $X_2$ is fluoro; and
$R_2$ is hydrogen.

3. The compound according to claim 2, or a pharmaceutically acceptable salt or hydrate thereof, where $R_1$ is imidazolyl, substituted with alkyl having 3 to 6 carbon atoms or phenyl.

4. The compound according to claim 2, or a pharmaceutically acceptable salt or hydrate thereof, where $R_1$ is pyrrolyl, optionally substituted with alkyl having 1 to 4 carbon atoms.

5. The compound according to claim 2, or a pharmaceutically acceptable salt or hydrate thereof, where $R_1$ is phenyl, substituted with amino, isoxazolyl, or morpholino.

6. The compound according to claim 2, or a pharmaceutically acceptable sail or hydrate thereof, where $R_1$ is phenyl, substituted with thiomorpholino, optionally substituted with oxo.

7. The compound according to claim 2, or a pharmaceutically acceptable salt or hydrate thereof, where $R_1$ is piperazine, substituted with alkyl having 1 to 4 carbon atoms or cyclohexyl.

8. The compound according to claim 2, or a pharmaceutically acceptable sail or hydrate thereof, where $R_1$ is thiomorpholino, optionally substituted with one or two oxos.

9. The compound according to claim 2, or a pharmaceutically acceptable salt or hydrate thereof, where $R_1$ is selected from the group consisting of indazolyl and cyclohexylamino.

10. The compound according to claim 1, or a pharmaceutically acceptable salt or hydrate thereof, which is selected from the group consisting of:
(E)-N-[2-(4-cyclohexylpiperazin-1-yl)ethyl]-3-(2-fluorophenyl)-2-propenamide,
(E)-N-[3-(4-cyclohexylpiperazin-1-yl)propyl]-3-(2-fluorophenyl)-2-propenamide,
(E)-3-(2-fluorophenyl)-N-[3-(4-methylpiperazin-1-yl)propyl]-2-propenamide,
(E)-3-(4-fluorophenyl)-N-(3-thiomorpholinopropyl)-2-propenamide,
(E)-3-(2-fluorophenyl)-N-(3-thiomorpholinopropyl)-2-propenamide,
(E)-N-[3-(1,1-dioxo-1,4-thiazinan-4-yl)propyl]-3-(2-fluorophenyl)-2-propenamide,
(E)-N-[3-(1,1-dioxo-1,4-thiazinan-4-yl)propyl]-3-(4-fluorophenyl)-2-propenamide,
(E)-3-(4-fluorophenyl)-N-[3-(1-oxo-1,4-thiazinan-4-yl)propyl]-2-propenamide, and
(E)-3-(2-fluorophenyl)-N-[3-(1-oxo-1,4-thiazinan-4-yl)propyl]-2-propenamide.

11. The compound according to claim 1, or a pharmaceutically acceptable salt or hydrate thereof, which is selected from the group consisting of:
(E)-3-(4-fluorophenyl)-N-(3-thiomorpholinopropyl)-2-propenamide,
(E)-3-(2-fluorophenyl)-N-(3-thiomorpholinopropyl)-2-propenamide,
(E)-3-(4-fluorophenyl)-N-[3-(1-oxo-1,4-thiazinan-4-yl)propyl]-2-propenamide, and
(E)-3-(2-fluorophenyl)-N-[3-(1-oxo-1,4-thiazinan-4-yl)propyl]-2-propenamide.

12. A pharmaceutical agent comprising, as an active ingredient, a compound of formula (I):

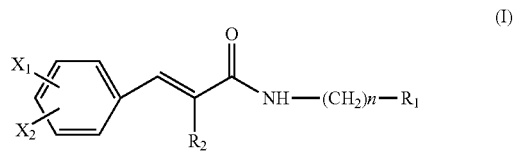

or a pharmaceutically acceptable salt or hydrate thereof, and a pharmaceutically acceptable carrier,
where:
n is 1, 2, 3, or 4;
each of $X_1$ and $X_2$ is independently selected from the group consisting of hydrogen, fluoro, trifluoromethyl, and carboxy, with the proviso that one of $X_1$ and $X_2$ is selected from the group consisting of fluoro, trifluoromethyl, and carboxy;

$R_1$ is selected from the group consisting of:
(1) imidazolyl, substituted with alkyl having 1 to 6 carbon atoms or phenyl;
(2) pyrrolyl, optionally substituted with alkyl having 1 to 4 carbon atoms;
(3) phenyl, substituted with amino, isoxazolyl, or morpholino;
(4) phenyl, substituted with thiomorpholino, optionally substituted with oxo;
(5) piperazino, substituted with alkyl having 1 to 4 carbon atoms or cyclohexyl;
(6) thiomorpholino, optionally substituted with one or two oxos; and
(7) benzoimidazolyl;
(8) indazolyl;
(9) pyrazolyl;
(10) triazolyl;
(11) pyrrolidinyl;
(12) piperidine;
(13) azepanyl;
(14) morpholino; and
(15) cyclohexylamino; and $R_2$ is selected from the group consisting of hydrogen, cyano, and alkyl having 1 to 4 carbon atoms.

13. The pharmaceutical agent according to claim 12, which is an oral preparation.

14. The pharmaceutical agent according to claim 12, which is an injectable preparation.

15. A method of treating pain in a subject comprising administering to a subject in need thereof an effective amount of the pharmaceutical agent according to claim 12.

16. The method according to claim 15, wherein the pain is neuropathic pain.

17. The method according to claim 15, wherein the pain is chronic pain.

18. The method according to claim 17, wherein the chronic pain is selected from the group consisting of lumbago, arthralgia, and neuropathic pain.

19. A compound, which is (E)-3-(2-fluorophenyl)-N-[3-(isoxazol-5-yl)phenyl]-2-propenamide.

* * * * *